United States Patent [19]

Haynor et al.

[11] Patent Number: 6,129,668
[45] Date of Patent: *Oct. 10, 2000

[54] SYSTEM AND METHOD TO DETERMINE THE LOCATION AND ORIENTATION OF AN INDWELLING MEDICAL DEVICE

[75] Inventors: David R. Haynor, Seattle; Christopher P. Somogyi, Woodinville; Robert N. Golden, Kirkland, all of Wash.

[73] Assignee: Lucent Medical Systems, Inc., Kirkland, Wash.

[*] Notice: This patent is subject to a terminal disclaimer.

[21] Appl. No.: 09/075,280

[22] Filed: May 8, 1998

Related U.S. Application Data

[63] Continuation-in-part of application No. 08/852,940, May 8, 1997.

[51] Int. Cl.$^7$ .................................................... A61B 5/05
[52] U.S. Cl. ........................ 600/424; 128/899; 600/408
[58] Field of Search ................................. 600/407, 424, 600/408; 128/899; 324/207.13, 207.17, 247, 207.11, 260

[56] References Cited

U.S. PATENT DOCUMENTS

| | | | |
|---|---|---|---|
| 3,648,908 | 3/1972 | Brown | 324/43 G |
| 3,757,773 | 9/1973 | Kolin | 128/2.05 F |
| 3,847,157 | 11/1974 | Caillouette et al. | 128/348 |
| 4,063,561 | 12/1977 | McKenna | 128/351 |
| 4,244,362 | 1/1981 | Anderson | 128/200.26 |
| 4,249,536 | 2/1981 | Vega | 128/349 B |

(List continued on next page.)

FOREIGN PATENT DOCUMENTS

| | | |
|---|---|---|
| 0 302 001 A1 | 2/1989 | European Pat. Off. |
| 29 03 357 A1 | 7/1980 | Germany. |
| 40 14 947 A1 | 11/1991 | Germany. |
| 02 021 290 | 3/1990 | Japan. |
| 2 102 127 | 1/1983 | United Kingdom. |
| 93 04628 | 3/1993 | WIPO. |
| 9608999 A1 | 3/1996 | WIPO. |
| WO 96/41119 | 12/1996 | WIPO. |
| WO 97/25101 | 7/1997 | WIPO. |
| WO 98/29033 | 7/1998 | WIPO. |

OTHER PUBLICATIONS

James, A. H., "Duodenal Intubation with Magnet-Tipped Tubes," *The Lancet:* 209–210, Jan. 27, 1951.

(List continued on next page.)

*Primary Examiner*—Marvin M. Lateef
*Assistant Examiner*—Shawna J. Shaw
*Attorney, Agent, or Firm*—Michael J. Donohue; Seed IP Law Group PLLC

[57] ABSTRACT

A device to detect the location of a magnet coupled to an indwelling medical device within a patient uses three or more sets of magnetic sensors each having sensor elements arranged in a known fashion. Each sensor element senses the magnetic field strength generated by the magnet and provides data indicative of the direction of the magnet in a three-dimensional space. The device uses fundamental equations for electricity and magnetism that relate measured magnetic field strength and magnetic field gradient to the location and strength of a magnetic dipole. The device uses an iterative process to determine the actual location and orientation of the magnet. An initial estimate of the location and orientation of the magnet results in the generation of predicted magnetic field values. The predicted magnetic field values are compared with the actual measured values provided by the magnetic sensors. Based on the difference between the predicted values and the measured values, the device estimates a new location of the magnet and calculates new predicted magnetic field strength values. This iteration process continues until the predicted values match the measured values within a desired degree of tolerance. At that point, the estimated location matches the actual location within a predetermined degree of tolerance. A two-dimensional display provides an indication of the location of the magnet with respect to the housing of the detector. A depth indicator portion of the display can be used to provide a relative or absolute indication of the depth of the magnet within the patient.

39 Claims, 13 Drawing Sheets

U.S. PATENT DOCUMENTS

| | | | |
|---|---|---|---|
| 4,317,078 | 2/1982 | Weed et al. | 324/208 |
| 4,402,310 | 9/1983 | Kimura | 128/4 |
| 4,608,992 | 9/1986 | Hakim et al. | 128/654 |
| 4,619,247 | 10/1986 | Inoue et al. | 128/6 |
| 4,622,644 | 11/1986 | Hansen | 364/559 |
| 4,671,287 | 6/1987 | Fiddian-Green | 128/631 |
| 4,788,975 | 12/1988 | Shturman et al. | 128/303.1 |
| 4,790,809 | 12/1988 | Kuntz | 604/8 |
| 4,809,713 | 3/1989 | Grayzel | 128/785 |
| 4,913,139 | 4/1990 | Ballew | 128/200.11 |
| 4,943,770 | 7/1990 | Ashley-Rollman et al. | 324/207.17 |
| 5,005,592 | 4/1991 | Cartmell | 128/899 |
| 5,042,486 | 8/1991 | Pfeiler et al. | 128/653 R |
| 5,099,845 | 3/1992 | Besz et al. | 128/653.1 |
| 5,134,370 | 7/1992 | Jefferts et al. | 324/247 |
| 5,222,501 | 6/1993 | Ideker et al. | 128/660.03 |
| 5,257,636 | 11/1993 | White | 128/897 |
| 5,325,873 | 7/1994 | Hirschi et al. | 128/899 |
| 5,377,678 | 1/1995 | Dumoulin et al. | 128/653.1 |
| 5,381,095 | 1/1995 | Andrews | 324/326 |
| 5,425,367 | 6/1995 | Shapiro et al. | 128/653.1 |
| 5,425,382 | 6/1995 | Golden et al. | 128/899 |
| 5,429,132 | 7/1995 | Guy et al. | 128/653.1 |
| 5,456,718 | 10/1995 | Szymaitis | 623/11 |
| 5,524,086 | 6/1996 | Kiyuna et al. | 364/527 |
| 5,526,812 | 6/1996 | Dumoulin et al. | 128/653.1 |
| 5,558,091 | 9/1996 | Acker et al. | 128/653.1 |
| 5,568,809 | 10/1996 | Ben-Haim | 128/656 |
| 5,622,169 | 4/1997 | Golden et al. | 128/653.1 |
| 5,624,430 | 4/1997 | Eton et al. | 606/1 |
| 5,645,065 | 7/1997 | Shapiro et al. | 128/653.1 |
| 5,731,996 | 3/1998 | Gilbert | 364/559 |
| 5,738,096 | 4/1998 | Ben-Haim | 128/653.1 |
| 5,752,513 | 5/1998 | Acker et al. . | |
| 5,762,064 | 6/1998 | Polvani | 128/653.1 |
| 5,769,843 | 6/1998 | Abela et al. | 606/10 |
| 5,845,646 | 12/1998 | Lemelson . | |
| 5,879,297 | 3/1999 | Haynor et al. . | |
| 5,902,238 | 5/1999 | Golden et al. | 600/424 |
| 5,913,820 | 6/1999 | Bladen et al. . | |
| 5,944,023 | 8/1999 | Johnson et al. | 128/899 |

OTHER PUBLICATIONS

Wenger et al., "Magnet–Tipped Tubes for Studies of the Stomach and Duodenum," *Digestive Diseases,* 15(4): 383–393, Apr. 1970.

Gaston et al., "External Magnetic Guidance of Endovascular Catheters with a Superconducting Magnet: Preliminary Trials," *Journal of Neuroradiology* 15(2):137–147, 1988.

Ram et al., "Heart Catherization in a Neonate by Interacting Magnetic Fields: A New and Simple Method of Catheter Guidance," *Catherization and Cardiovascular Diagnosis* 22(4):317–319, Apr. 1991.

Williams et al. Abstract, "The Localisation of Enteral Tubes Using a Novel Non–Radiological Technique ("Cathlocator")," *British Society of Gastroenterology,* Mar. 1992.

Weitschies et al., "Magnetic Markers as a Noninvasive Tool to Monitor Gastrointestinal Transit," *IEEE Transactions on Biomedical Engineering,* 41(2):192–195, Feb. 1994.

SYSTEM AND METHOD TO DETERMINE THE LOCATION AND ORIENTATION OF AN INDWELLING MEDICAL DEVICE

CROSS-REFERENCE TO RELATED APPLICATION

This application is a continuation-in-part of U.S. patent application Ser. No. 08/852,940, Filed May 8, 1997, now pending.

STATEMENT OF GOVERNMENT INTEREST

This invention was made with government support under SBIR Grant No. RR10676-03 awarded by the National Center for Research Resources of the National Institutes of Health. The government has certain rights in this invention.

TECHNICAL FIELD

This invention is generally directed to a system and method for detecting the location of an indwelling medical device within the body of a patient and, more specifically, to a detection apparatus which senses magnetic field strength generated by a magnet associated with the indwelling medical device.

BACKGROUND OF THE INVENTION

There are many instances in clinical medicine where detecting the location of a medical tube within a patient is important. For example, when positioning feeding tubes through the mouth or nose of a patient, it is essential that the end of the feeding tube pass into the patient's stomach, and that it does not "curl up" and remain in the esophagus. If the end of the feeding tube is not properly positioned within the stomach, aspiration of the feeding solution into the patient's lungs may occur. In addition to feeding tubes, a variety of other medical tubes require accurate positioning within a patient's body, including dilating tubes to widen an esophageal stricture, tubes for measuring pressure waves in the stomach and esophagus of a patient who is suspected of having esophageal motor disorders, Sengstaken-Blakemore tubes in the stomach and esophagus of a patient to control bleeding from varicose veins in the esophagus, colonic decompression tubes in the colon of a patient to assist in relieving distention of the colon by gas, urologic tubes in the bladder, ureter or kidney of a patient, laser tubes inserted into the heart for transmyocardial revascularization, and vascular tubes in the heart or pulmonary arteries of a patient.

Currently, the location of a medical tube within the body of a patient is routinely detected by the use of imaging equipment, such as a chest or abdominal X-ray. However, such a procedure requires transportation of the patient to an X-ray facility or, conversely, transportation of the X-ray equipment to the patient. This is both inconvenient and costly to the patient, and is particularly stressful in those instances where the patient repeatedly and inadvertently removes a medical tube, such as a feeding tube, thus requiring repeated reinsertion and X-rays.

Prior attempts at detecting the location of medical tubes within a patient have met with only limited success. For example, in U.S. Pat. No. 5,099,845 to Besz et al., a transmitter is located within a catheter, and an external receiver, tuned to the frequency of the transmitter, is used to detect the location of the catheter within the patient. This approach, however, requires either an external or internal power source to drive the transmitter. An external power source adds significant risk associated with shock or electrocution, and requires that electrical connections be made prior to positioning of the catheter within the patient. An internal power source, such as a battery, must be relatively small and can only provide power to the transmitter for a limited time. This precludes long-term detection of the catheter's location, and poses additional risks associated with placing a battery internally in a patient, such as the risk of battery leakage or rupture. In addition, the transmitter is relatively complex, and requires an active electronic circuit (either internal or external to the catheter), as well as the various wires and connections necessary for its proper function. Lastly, the signal produced by the transmitter is attenuated differently by different body tissues and bone. This attenuation requires adjustments in the transmitter's signal strength and frequency depending on the location of the catheter within the patient's body.

A further attempt at detecting the location of medical tubes within a patient is disclosed in U.S. Pat. No. 4,809,713 to Grayzel. There, an electrical cardiac-pacing catheter is held in place against the inner heart wall of a patient by the attraction between a small magnet located in the tip of the pacing catheter and a large magnet located on (e.g., sewn into) the patient's chest wall. An indexed, gimbaled, three-dimensional compass is used to determine the best location for the large magnet. The compass' operation relies upon the torque generated by the magnetic forces between the small magnet and the magnetized compass pointer in order to point the compass towards the small magnet. However, this compass will simultaneously try to orient itself to the Earth's ambient magnetic field. Because of this, the forces between the small magnet and the magnetized compass pointer at distances greater than several centimeters are not strong enough to accurately orient the compass towards the small magnet. Furthermore, although the compass aids positioning of the large magnet, positioning of the small magnet, and hence the pacing catheter, still requires the use of imaging equipment, such as X-ray or ultrasound.

For the foregoing reasons, there is a need in the art for a medical tube, apparatus and method for detecting the location of the medical tube within the body of a patient which avoids the problems inherent in existing techniques. The medical tube, apparatus and method should provide for the detection of the medical tube at distances ranging from several centimeters to several decimeters, should not require the medical tube to have an internal or external power source, and should obviate the need to independently verify positioning of the medical tube with imaging equipment.

SUMMARY OF THE INVENTION

The present invention is embodied in a system and method for the detection of a position of a magnet associated with an indwelling medical device. The system includes a plurality of magnetic sensors that each generate a set of signals as a function of the magnetic field strength generated from the magnet and a direction from the sensor to the magnet. A processor calculates a predicted position of the magnet in a 3-dimensional space and calculates a predicted value related to magnetic field strength of the magnet at the predicted location. The processor calculates an actual value related to the magnetic field strength of the magnet using signals generated by the magnetic sensors and determines the location of the magnet in the 3-dimensional space based on the difference between the predicted value and the actual value. The system may also include a neural network to generate the estimated position based on the set of signals generated by the magnetic sensors. In one embodiment, the processor performs an iterative process of calculating the predicted position and predicted value related to the magnetic field and alters the predicted position based on the difference between the predicted value and the actual value. The iterative process continues until the predicted value and the actual value match each other within a predetermined tolerance. The system also includes a display to provide a visual display of data related to the position of the magnet in the 3-dimensional space. With the iterative process, the system must first generate an initial estimate. The neural network may be used to generate the initial estimate based on the signals generated by the magnetic sensors.

In one embodiment, the display is a two-dimensional display indicating the position of the magnet with respect to the housing. A depth indicator portion of the two-dimensional display provides an indication of the distance of the magnet from the housing. The display can include a visual indicator to assist the care giver in centering the housing over the magnet. In one embodiment, the display is integral with the housing and includes a transparent portion to permit viewing of the patient below the housing. Alternatively, the display may be an external display electrically coupled to the measurement device. With an external display, the data related to the position of the magnet may be combined with an image of the interior anatomy of the patient generate by a conventional imaging device, such as a fluoroscope, X-ray, MRI, and the like.

The sensors themselves can be selected from a group of magnetic sensors comprising Hall-effect sensors, flux-gate sensors, wound-core inductive sensors, squid sensors, magneto-resistive sensors, and nuclear precession sensors.

The system may further include a position detection system, such as a digitizing arm, to determine the location of the measurement device. In this embodiment, the device may be readily moved by the caregiver with the new location of the device being provided by the position detection system. Based on position data provided by the position detection system, the calibration processor may recalibrate the system even in the presence of the magnet. In this embodiment, the effects of the magnet are subtracted by calculating the contribution to the actual magnetic field measured by the magnetic sensors at the new location. The calibration determines the effects of the Earth's magnetic field at the new location based on the difference between the actual magnetic field measured by the magnetic sensors and the contribution to the actual magnetic field resulting from the magnet. The position detecting system may also be used to provide landmarks to the user. Prior to detection of the magnet, the user may indicate one or more landmark positions using the position detection system. In subsequent operation, as the magnet is inserted into the patient, the predetermined landmarks are shown on the display along with data relating to the position of the magnet. This permits the user to monitor the insertion of the catheter along the route marked by the landmarks.

The magnet has a magnetic dipole moment indicative of the orientation of the magnet. The sensors can detect the magnetic dipole moment and provide a visual indication on the display to indicate the magnet orientation.

In one embodiment, each sensor comprises first, second, and third sensor elements arranged in an orthogonal fashion to detect magnetic field strength in three dimensions corresponding to the first, second, and third orthogonally arranged sensor elements.

DETAILED DESCRIPTION OF THE INVENTION

The present invention provides a medical tube, apparatus and method for detecting the location of the medical tube within the body of a patient. As used herein, the term "medical tube" means any type of tube or device which may be inserted into a patient's body, including (but not limited to) catheters, guide wires, and medical instruments. For example, catheters include such items as feeding tubes, urinary catheters, guide wires and dilating catheters, as well as nasogastric tubes, endotracheal tubes, stomach pump tubes, wound drain tubes, rectal tubes, vascular tubes, Sengstaken-Blakemore tubes, colonic decompression tubes, pH catheters, motility catheters, and urological tubes. Guide wires are often used to guide or place dilators and other medical tubes. Medical instruments include lasers, endoscopes and colonoscopes. In short, the location of any foreign object within a patient's body is a suitable device for detection by the present invention, and is encompassed within the term "medical tube."

The present invention detects the location of the medical tube by sensing the magnetic field produced by a permanent magnet associated with the medical tube. As used herein, the term "associated with" means permanently fixed, removably attached, or in close proximity with, the medical tube. In one embodiment, such as a feeding tube, the magnet is associated with the end of the medical tube. In another embodiment, such as a Sengstaken-Blakemore tube, the magnet is associated with the medical tube at a location above the gastric balloon. Preferably, the magnet is a small, cylindrical, rotatably attached, rare-Earth magnet. Suitable magnets include rare Earth magnets such as samarium cobalt and neodymium iron boron, both of which generate high field strengths per unit volume. While magnets which generate a high field strength for their size are preferred, weaker magnets such as Alnico or ceramic may also be utilized.

Since the magnet is permanent, it requires no power source. Accordingly, the magnet maintains its magnetic field indefinitely, which allows long-term positioning and detection of medical tubes without the disadvantages associated with an internal or external power source. In particular, by avoiding the use of a power source, the undesirable electrical connections necessary for the use of a power source are avoided. Thus, there is no risk of electric shock to (or possible electrocution of) the patient. Furthermore, the magnet's static magnetic field passes unattenuated through body tissue and bone. This property allows the use of the present invention to detect the medical tube at any location within the patient's body.

Figure 1:
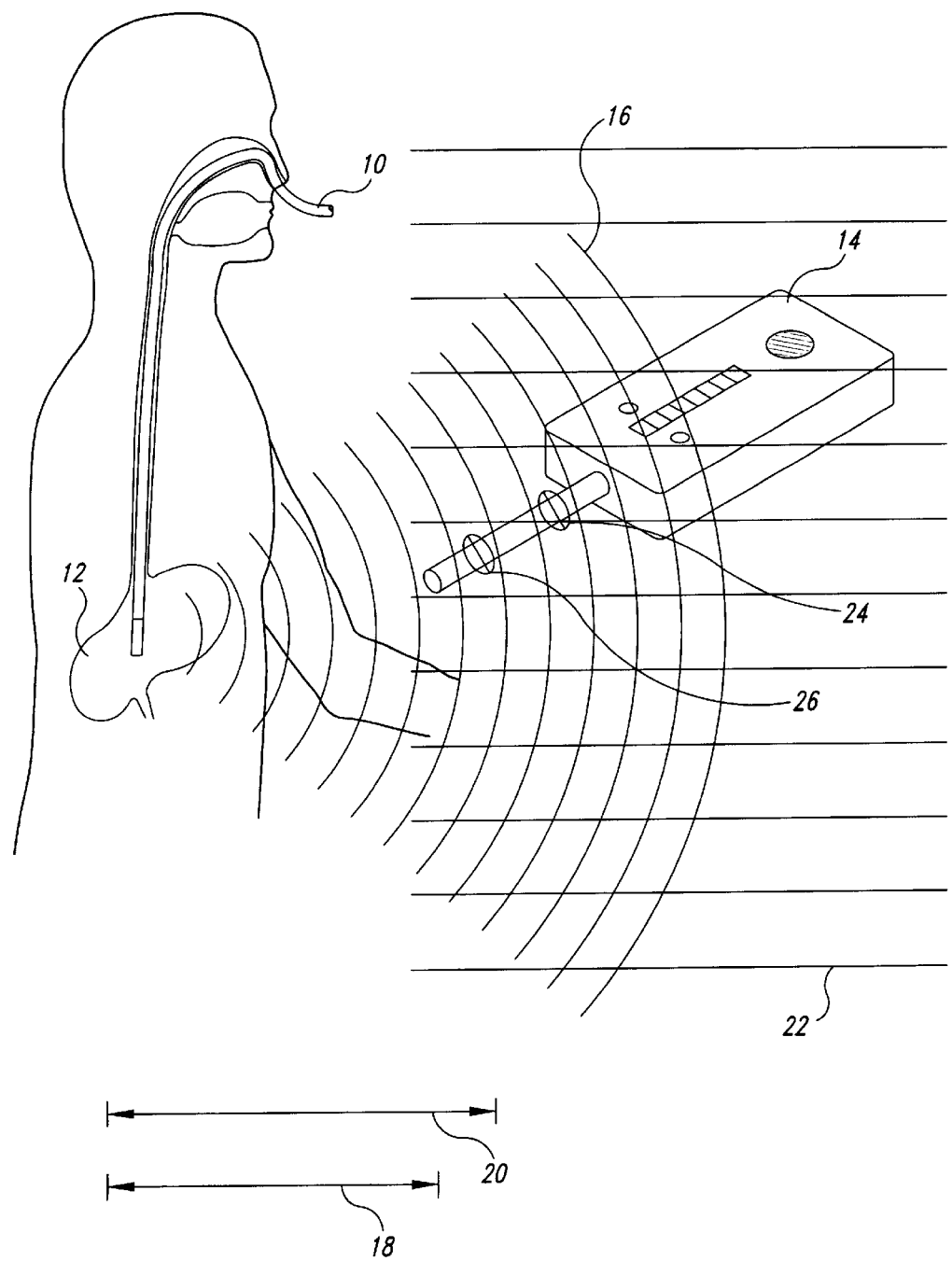
FIG. 1 illustrates the location of a magnet fixed to the end of a medical tube positioned within the body of a human patient using a known detection apparatus.

One known technique for locating a medical tube in the body of a patient is described in U.S. Pat. No. 5,425,382, which is incorporated herein by reference in its entirety. FIG. 1 illustrates the techniques described in U.S. Pat. No. 5,425,382. A tube 10, with a permanent magnet 12 located in its tip is inserted into the patient. In the example illustrated in FIG. 1, the tube 10 is a feeding tube that is inserted into the patient's nose, down the esophagus, and into the stomach. However, the system may be readily used with other types of tubes. A detection apparatus 14 is used to sense the magnet's static magnetic field strength 16 at two different distances 18 and 20 while immersed in the Earth's ambient magnetic field 22. By measuring the static magnetic field strength 16 at two different distances 18 and 20, the detection apparatus 14 determines the magnetic field gradient. As the detection apparatus 14 is moved about the patient's body, greater and lesser magnetic field gradients are indicated. The tube 10 is located by moving the detection apparatus 14 until the greatest magnitude is indicated by the detection apparatus.

Figure 2:
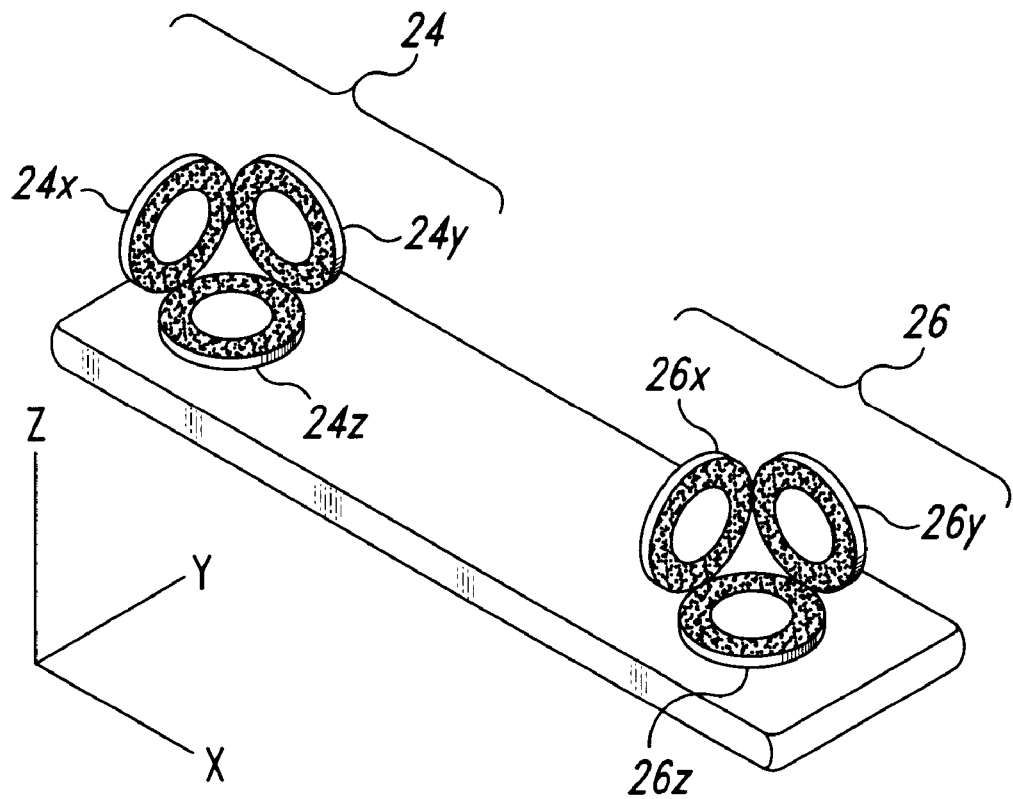
FIG. 2 illustrates the orientation of the x, y and z magnetic sensors used in a known detection apparatus.

The detection apparatus 14 described in U.S. Pat. No. 5,425,382 utilizes first and second magnetic sensors 24 and 26, respectively. As described in that patent, the magnetic sensors 24 and 26 may each comprise flux-gate toroidal sensors to detect the magnetic field gradient. An alternative magnetic field gradient detector system is described in U.S. Pat. No. 5,622,169, which is incorporated herein by reference in its entirety. FIG. 2 illustrates the magnetic sensor arrangement described in U.S. Pat. No. 5,622,169. The magnetic sensors 24 and 26 each comprise three orthogonally arranged flux-gate toroidal sensor elements. The magnetic sensor 24 comprises magnetic sensor elements $24x$, $24y$, and $24z$ that are orthogonally arranged to measure magnetic field strength in three orthogonal directions, illustrated in FIG. 2 by x, y, and z axes, respectively. Similarly, the magnetic sensor 26 comprises magnetic sensor elements $26x$, $26y$, and $26z$ to measure magnetic field strength in the x, y, and z directions, respectively. Using the sensors 24 and 26, the magnetic field gradient may be determined in the x, y, and z directions. With measurements of magnetic field gradient in three directions, the location of the magnet 12 (see FIG. 1) may be readily determined using conventional vector mathematics. The mathematical sign of the magnetic gradient is indicative of the direction of the magnetic field dipole of the magnet 12.

The magnet, and hence the medical tube, is detected using a known detection apparatus that contains at least two static magnetic field strength sensors configured geometrically to null detection of ambient, homogeneous magnetic fields (e.g., the Earth's field), while still detecting the magnetic field strength gradient produced by the magnet.

The magnet detection apparatus illustrated in FIGS. 1 and 2 detects the location of the magnet based on the difference in magnetic field strength at the two sensors. However, it is possible to construct a magnetic field detection apparatus with different sensor configurations to provide additional data related to the position and orientation of the magnet. The present invention is directed to a technique for detection of a magnet using a multisensor array and a convergence algorithm that can accurately locate the position of the magnet in three dimensions. An exemplary embodiment of the invention is embodied in a detector system 100, shown in FIG. 3. The detector system 100 includes a housing 102, control switches 104 such as a power switch and a reset switch, and a display 106. In an exemplary embodiment, the display 106 is a two-dimensional liquid crystal display. The display 106 may have an opaque background, or have a transparent area which allows the caregiver to view the skin below the surface of the detector system 100. As will be discussed in greater detail below, the ability to view external patient landmarks significantly aids in the placement of catheters using the detector system 100. Alternatively, the display 106 may be an external display such as a video monitor.

Also mounted within the housing 102 are first, second, third, and fourth magnetic sensors 108, 110, 112, and 114, respectively. In a preferred embodiment, the static magnetic sensors 108–112 are spaced to provide maximal separation within the housing 102. In an exemplary embodiment, the magnetic sensors 108–112 are arranged in a substantially planar fashion within the housing 102 and located proximate the corners of the housing.

Figure 3:
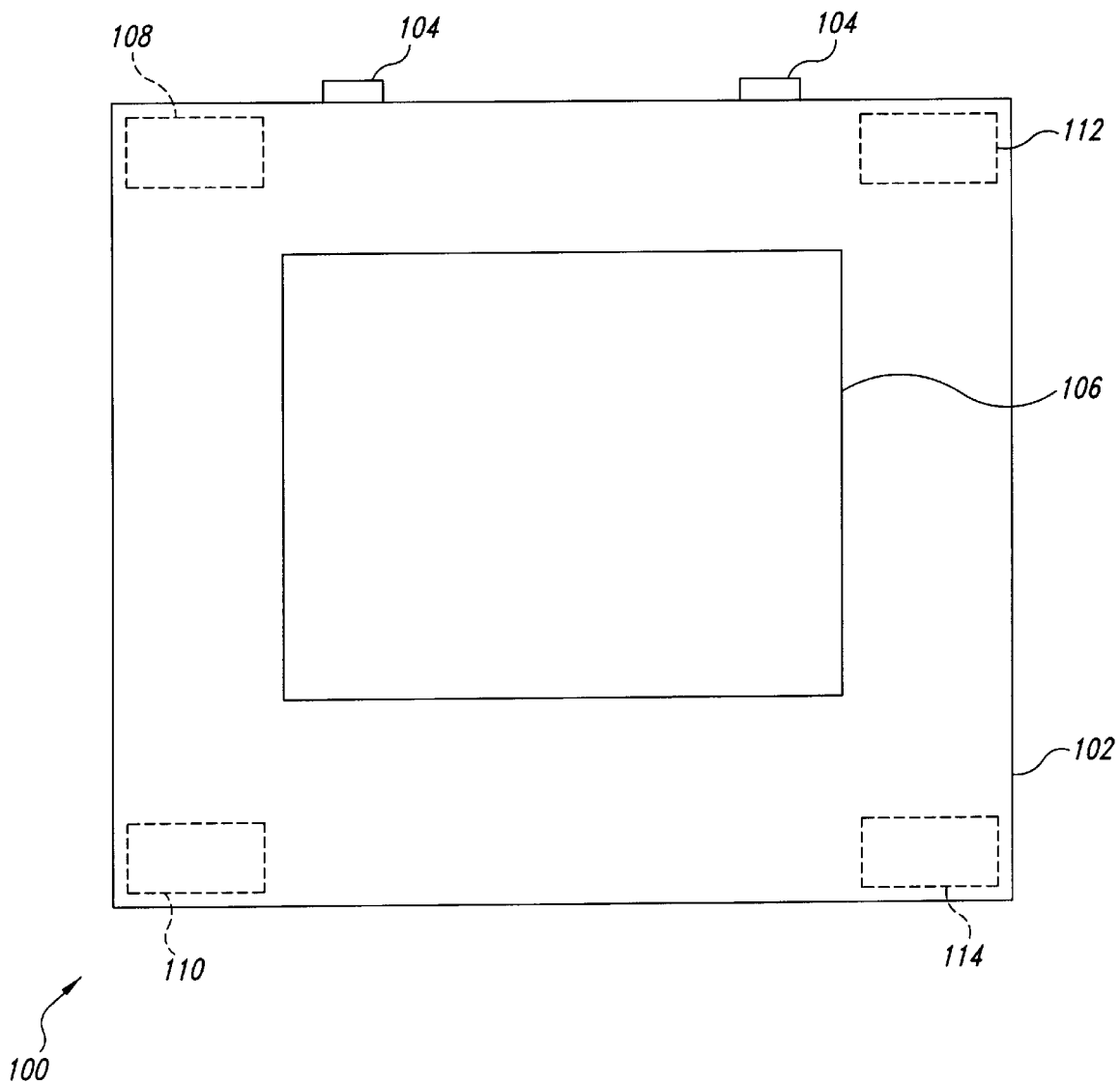
FIG. 3 is a top plan view of the detector of the present invention illustrating one possible arrangement of magnetic sensors.
Figure 4:
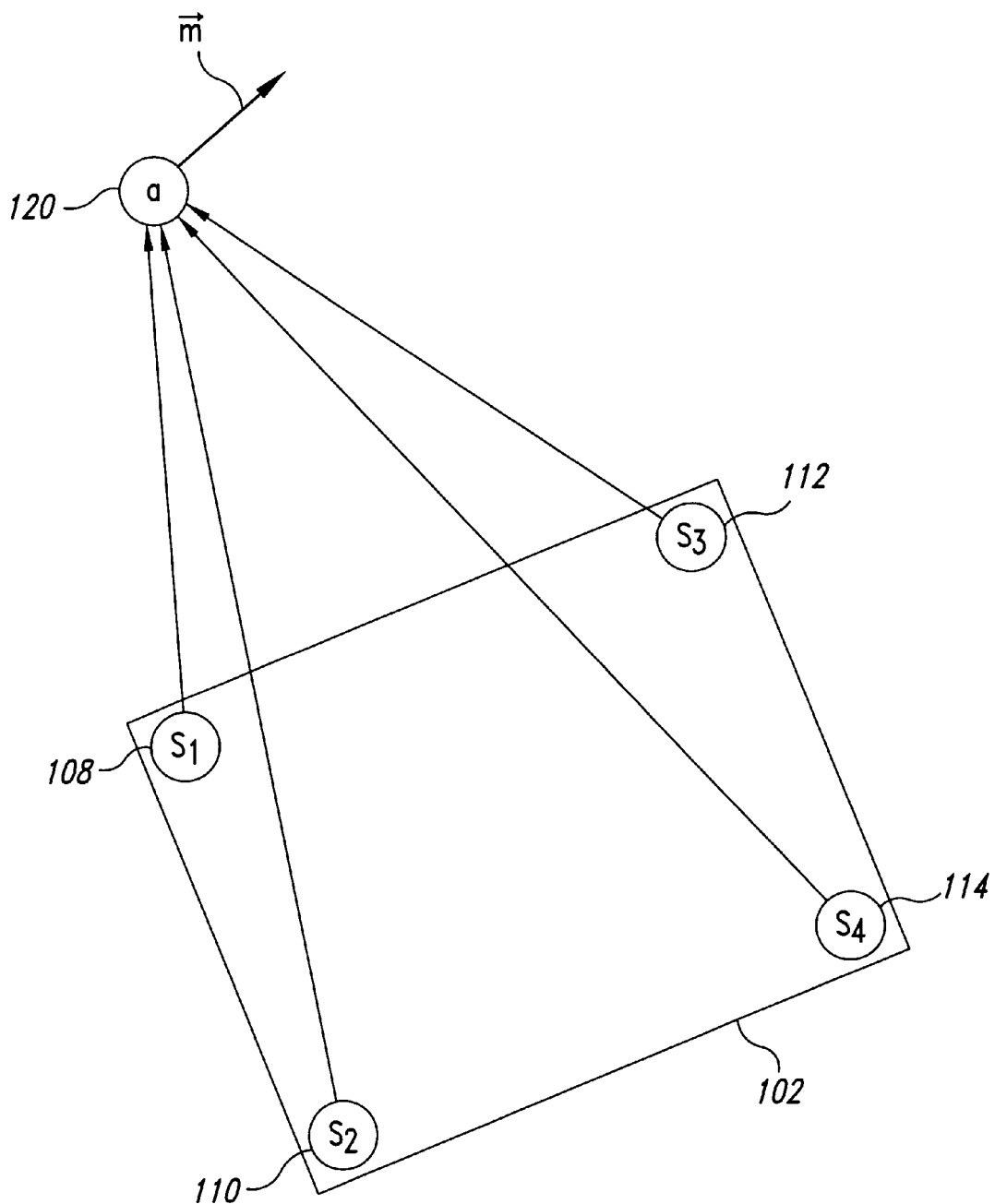
FIG. 4 illustrates the generation of magnetic field strength vectors using the magnetic sensor configuration of FIG. 3 to determine the location of a magnet.

The orientation of the magnetic sensors 108–114 is illustrated in FIG. 4 where the magnetic sensors 108–114 are positioned at locations $S_1$ to $S_4$, respectively, near the corners of the housing 102. Although the system 100 described in FIGS. 3 and 4 illustrates a rectangular configuration for the magnetic sensors 108–114, the principles of the present invention are readily applicable to any multi-sensor array. Accordingly, the present invention is not limited by the specific physical arrangement of the magnetic sensors.

In an exemplary embodiment, each of the magnetic sensors 108–114 comprise three independent magnetic sensing elements orthogonally arranged to provide three-dimensional measurement in the x, y, and z directions, such as illustrated in FIG. 2. The sensing elements of the magnetic sensors 108–114 are aligned with respect to a common origin such that each magnetic sensor senses the static magnetic field in the same x, y and z directions. This permits the detection of magnetic field strength in a three-dimensional space by each of the magnetic sensors 108–114. The arrangement of the magnetic sensors 108–114 permits the detection of a magnet in a three-dimensional space within the patient. That is, in addition to locating the magnet within the patient, the detector system 100 provides depth information.

The configuration of the magnetic sensors 108–114 can be readily changed for specialized application. For example, a plurality of magnetic sensors may be configured in a spherical arrangement around a patient's head to detect the location of the magnet 120 in the brain. Furthermore, the magnetic sensing elements need not be orthogonally arranged. For example, the magnetic sensing elements may be configured in a planar array or other convenient configuration suited to the particular application (e.g., the spherical arrangement). The only requirement for satisfactory operation of the detector system 100 is that the detector system must have at least as many sensing elements to provide data as there are unknowns in the equations to be solved and that the location and orientation of the magnetic sensing elements be known.

In the present case, it is desirable to detect the position and orientation of the magnet 120 in three dimensional space. This results in five unknown parameters, that may conveniently be considered as x, y, z, $\theta$ and $\phi$ where x, y, and z represent coordinates of the magnet 120 in three dimensional space relative to an origin such as the center of the housing 102, $\theta$ is the angular orientation of the magnet in the YZ plane and $\phi$ is the angular orientation of the magnet in the XY plane. In addition, the contribution of the Earth's magnetic field in the x, y, and z directions is unknown. Thus, the model used by the detector system 100 has eight unknown parameters that require eight independent measurements. In an exemplary embodiment of the detector system 100 described herein, a set of twelve magnetic sensing elements is used to provide over sampling. This results in greater reliability and accuracy while maintaining the computational requirements at a reasonable level.

The mathematical description provided below may be most easily understood with respect to a Cartesian coordinate system using magnetic sensing elements orthogonally arranged in the x, y, and z directions. However, it should be clearly understood that the present invention is not limited to such an arrangement. Any alignment of the magnetic sensing elements may be used with the detector system 100 so long as the location and orientation of the magnetic sensors 108–114 are known. Therefore, the present invention is not limited by the specific configuration of magnetic sensing elements.

As illustrated in FIG. 4, a magnet 120 is positioned at a location a. As is known in the art, the magnet 120 has a magnetic dipole that is represented by the vector m. The vector m represents the strength and orientation of the magnetic dipole. Under ideal conditions, the magnetic sensors 108–114 can measure the static magnetic field generated by the magnet 120 and determine the location of the magnet at location a with a single measurement. However, the presence of the Earth's magnetic field, stray magnetic fields that may be present near the vicinity of the magnet 120, internal noise from the magnet sensors 108–114, internal noise generated by electronics associated with the magnetic sensors, such as amplifiers and the like, make it virtually impossible to perform a measurement under "ideal" conditions. To provide accurate positional information for the magnet 120 in the presence of various forms of noise, the detector system 100 uses known formulas for magnetic field strength, plus actual sensor measurements as inputs to an estimation algorithm that converges to provide an accurate reading of the location and orientation of the magnet 120.

Figure 5A:
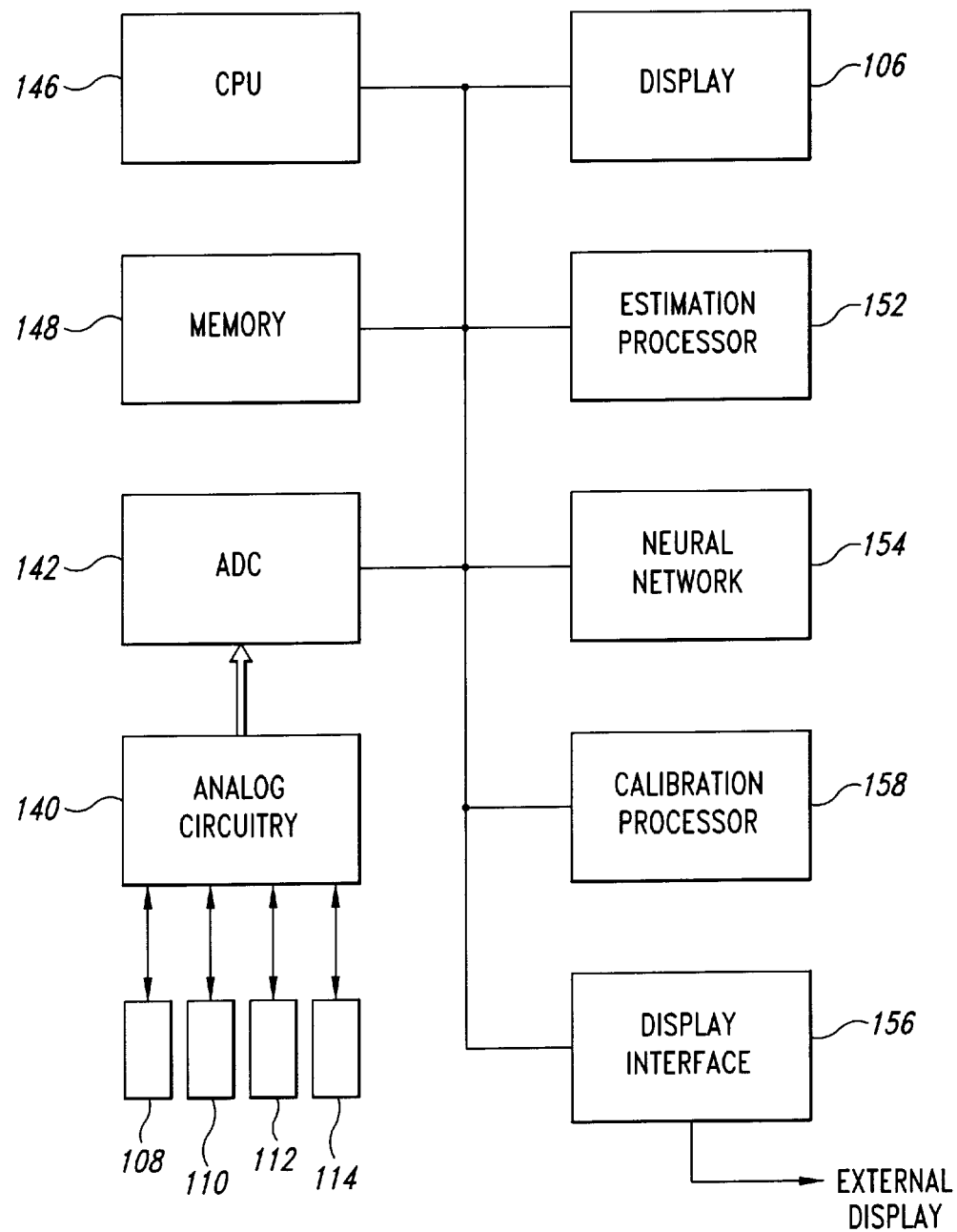
FIG. 5A is a functional block diagram of an exemplary embodiment of a system constructed in accordance with the present invention to determine the location of a magnet.

The elements used to process data from the magnetic sensor 108–114 are illustrated in a functional block diagram of FIG. 5A where the magnetic sensors 108–114 are coupled to analog circuitry 140. The specific form of the analog circuitry 140 depends on the specific form of the magnetic sensors 108–114. For example, if the magnetic sensors 108–114 are orthogonally positioned flux-gate toroidal sensors, similar to those illustrated in FIG. 2, the analog circuitry 140 may include amplifiers and integrators such as discussed in U.S. Pat. Nos. 5,425,382 and 5,622,669. In another exemplary embodiment, the magnetic sensors 108–114 comprise magneto-resistive elements whose resistance varies with the strength of a magnetic field. Each magnetic sensors 108–114 comprises three orthogonally arranged magneto-resistive sensing elements to sense the static magnetic field in the x, y, and z directions, respectively.

However, the magnetic sensors 108–114 may be any form of magnetic sensor. Several different types of magnetic sensors may be used in the practice of the present invention, including, but not limited to, Hall-effect, flux-gate, wound-core inductive, squid, magneto-resistive, nuclear precession sensors, and the like. Commercial magnetic field gradient sensors in the form of an integrated circuit can also be used with the detector system 100. Furthermore, the magnetic sensors 108–114 need not be identical types of sensors. For example, the magnetic sensors 108–112 may be one type of sensor while the magnetic sensor 114 may be a different type.

The analog circuitry 140 is designed to operate with the specific form of the magnetic sensors 108–114. The specific design of the analog circuitry 140 is well within the knowledge of one of ordinary skill in the art and need not be described in greater detail herein.

The output of the analog circuitry 140 is coupled to an analog-to-digital converter (ADC) 142. The ADC 142 converts the analog output signals from the analog circuitry 140 to a digital form. The operation of the ADC 142 is well known to those of ordinary skill in the art and will not be described in detail herein. The detector system 100 also includes a central processing unit (CPU) 146 and a memory 148. In an exemplary embodiment, the CPU 146 is a microprocessor, such as a Pentium™ or the like. The memory 148 may include both read-only memory and random access memory. The various components, such as the ADC 142, CPU 146, memory 148, and display 106 are coupled together by a bus system 150. As can be appreciated by those of ordinary skill in the art, the bus system 150 illustrates a typical computer bus system and may carry power and control signals in addition to data.

Also illustrated in the functional block diagram of FIG. 5A is an estimation processor 152. As will be described in greater detail below, the estimation processor 152 performs an iterative comparison between an estimated position of the magnet 120 (see FIG. 2) and a measured position of the magnet 120 based on data derived from the magnetic sensors 108–114. The iterative process continues until the estimated position and the measured position converge, resulting in an accurate measurement of the location a (see FIG. 4) of the magnet 120. It should be noted that the estimation processor 152 is preferably implemented by computer instructions stored in the memory 148 and executed by the CPU 146. However, for the sake of clarity, the functional block diagram of FIG. 5A illustrates the estimation processor 152 as an independent block since it performs an independent function. Alternatively, the estimation processor 152 can be implemented by other conventional computer components, such as a digital signal processor (not shown).

The detector system 100 assumes that the magnetic sensors 108–114 are sufficiently far from the location a of the magnet 120 that the magnet may be treated as a point dipole source. In addition, it is assumed that the spatial variation of any extraneous magnetic fields, such as the Earth's magnetic field, is small compared to the inhomogeneity produced by the presence of the point dipole source. However, under some circumstances, perturbations in the Earth's magnetic field may be caused by extraneous sources such as nearby electrical equipment, metallic building structural elements, and the like. As will be discussed in detail below, the detector system 100 can be readily calibrated to compensate for such perturbations.

The equations used by the estimation processor 152 are readily derived from the fundamental laws of physics related to electricity and magnetism. A static magnetic field B produced by the magnetic dipole of a strength m, and situated at a location a, and measured at a location s is given by the following:

$$B(s) = \frac{3((s-a) \cdot m)(s-a) - \|s-a\|^2 m}{\|s-a\|^5} \quad (1)$$

where $\|s-a\|$ is a modulus value well known in matrix mathematics (e.g., $\|s-a\|^2$ is a square modulus). It should be noted that the values a, m, s, and B are all vector values. The term "static magnetic field" is intended to describe the magnetic field generated by the magnet 120, as opposed to a time varying electromagnetic field or an alternating magnetic field. The magnet 120 generates a fixed, constant (i.e., static) magnetic field. The strength of the magnetic field detected by the detector system 100 depends on the distance between the magnet 120 and the magnetic sensors 108–114. Those skilled in the art can appreciate that the detected magnetic field strength may vary as the magnet 120 is moved within the patient or as the detector system 100 is moved with respect to the magnet. However, relative movement between the detector system 100 and the magnet 120 is not essential. The detector system 100 can readily determine the location and orientation of the magnet 120 in three-dimensional space even when the detector system and the magnet are not moving with respect to each other.

The values from the magnetic sensors 108–114 can be used in equation (1) to determine the strength of the magnetic field B at locations S1–S4, respectively. Changes in the magnetic field B over distance is defined as a gradient G(s) of B, which is a derivative of B with respect to s. The gradient G(s) can be represented by a 3×3 matrix derived from equation (1) and expressed in the following form:

$$G(s) = \frac{-(15((s-a) \cdot m))(s-a)(s-a)^T + 3\|s-a\|^2((s-a)m^T + m(s-a)^T + ((s-a) \cdot m)I)}{\|s-a\|^7} \quad (2)$$

where T is a matrix transpose and I is a 3×3 identity matrix having the following form:

$$I = \begin{bmatrix} 1 & 0 & 0 \\ 0 & 1 & 0 \\ 0 & 0 & 1 \end{bmatrix}$$

It should be noted that equation (1) could be solved directly for the value a given the values B, m, and s. However, such a calculation can be difficult to solve and may require significant computing power. The iterative estimation process described below determines the location a and orientation of the magnet 120 by estimating the location a and comparing a predicted or estimated magnetic field that would result from the magnet 120 being located at the estimated location with the actual measured magnetic field as measured by the magnetic sensors 108–114. The iterative process varies the estimated location in a controlled manner until the predicted magnetic field closely matches the measured magnetic field. At that point, the estimated location and orientation matches the actual location a and orientation of the magnet 120. Such an iterative process can be performed very quickly by the detector system 100 without the need for extensive computational calculations required to solve for the location a directly using equation (1). The difference between the predicted magnetic field and the actual measured magnetic field is an error, or error function, that may be used to quantitatively determine the location a of the magnet 120. The error function is used in the iterative process to refine the estimated location of the magnet 120. Equation (2), indicating the gradient G(s) is used by the estimation processor 152 (see FIG. 5A) to determine the magnitude and a direction of error in the estimated location. Thus, equation (1) is used to generate predicted values and equation (2) uses the error results to determine how to alter the estimated position of the magnet 120.

The magnetic field strength B is measured at each of the locations $S_1$–$S_4$ by the magnetic sensors 108–114, respectively. While only four magnetic sensors are illustrated in FIG. 3 to FIG. 5A, the measurement may be generalized to n sensors such that each of the magnetic sensors provides a measurement of $B(s_i)$ at points $s_i$, where i=1 to n. The estimation processor 152 calculates quantities $\Delta_{ij}$ (measured)=$B(s_i)$–$B(s_j)$. This calculation provides a measure of the gradient from magnetic sensor i to magnetic sensor j and also cancels out the effects of the Earth's magnetic field, which is constant (i.e., gradient=0) at the magnetic sensor i and the magnetic sensor j. The estimation processor 152 also calculates predicted values $\Delta_{ij}$ (predicted) from equation (1). The estimate for the value a is adjusted until the measured values $\Delta_{ij}$ (measured) and predicted values $\Delta_{ij}$ (predicted) match as closely as possible. For example, the detector system 100 may initially assume that the location a of the magnet 120 is centered under the housing 102. Based on this estimated location, the estimation processor 152 calculates the predicted values for magnetic field strength at each of the magnetic sensors 108–114 that would result if the magnet 120 were actually at the estimated location. In an exemplary embodiment, the sensing elements of each of the magnetic sensors 108–114 provide a measure of the magnetic field B in three orthogonal directions resulting in magnetic field strength values $B_{xi}$, $B_{yi}$, and $B_{zi}$ where i equals 1 to n. Similarly, the gradient G(s) is also calculated for each of the three orthogonal directions.

The estimation processor 152 also uses measured magnetic field strength values from each of the magnetic sensors 108–114 and compares $\Delta_{ij}$ (predicted) with $\Delta_{ij}$ (measured). Based on the difference between $\Delta_{ij}$ (predicted) and $\Delta_{ij}$ (measured), the estimation processor 152 generates a new estimated location for the magnet 120 (see FIG. 4) and iterates the prediction process until $\Delta_{ij}$ (predicted) closely matches $\Delta_{ij}$ (measured).

The degree of match between $\Delta_{ij}$ (predicted) and $\Delta_{ij}$ (measured) may be measured by a cost function comprising the sum of the squares of the difference between $\Delta_{ij}$ (predicted) and $\Delta_{ij}$ (measured) and then using non-linear iterative optimization algorithms to minimize the value of the cost function. The required gradients of the cost function are calculated using equation (2) above. Many different, well-known cost functions and/or optimization techniques, such as neural networks, may be used by the estimation processor 152 to achieve the desired degree of match between $\Delta_{ij}$ (predicted) and $\Delta_{ij}$ (measured).

The iterative measuring process performed by the estimation processor 152 can be done in a short period of time. A typical measurement cycle is performed in fractions of a second. As the tube and associated magnet 120 are moved within the patient, the position and orientation of the magnet will change. However, because the measurement cycle is very short, the change in position and orientation of the magnet will be very small during any given measurement cycle, thus facilitating real-time tracking of the magnet as the magnet is moved inside the patient or as the housing 102 is moved on the surface of the patient.

As discussed above, the estimation processor performs an iterative comparison between an estimated position of the magnet and a measured position of the magnet. The initial estimated location may be derived by a number of possible techniques, such as random selection, a location under the sensor element 108–114 having the strongest initial reading, or, by way of example, the detector system 100 may initially estimate the location a of the magnet 120 is centered under the housing 102. However, it is possible to provide a more accurate initial estimation of the location a of the magnet 120 using a neural network 154, shown in FIG. 5A. It should be noted that the neural network 154 is preferably implemented by computer instructions stored in the memory 148 and executed by the CPU 146. However, for the sake of clarity, the functional block diagram of FIG. 5A illustrates the neural network 154 as an independent block since it performs an independent function. Alternatively, the neural network 154 can be implemented by other conventional computer components, such as a digital signal processor (not shown).

Neural networks are capable of receiving and processing large amounts of data and, by virtue of a learning process, determining which data are more important. The operation of a neural network is generally known in the art, and thus will be described herein only with respect to the specific application. That is, the operation of the neural network 154 to generate an initial position estimate will be discussed.

The neural network 154 has a learn mode and an operational mode. In the learn mode, the neural network 154 is provided with actual measurement data from the magnetic sensors 108–114. Since each of the magnetic sensors 108–114 have three different sensing elements, a total of 12 parameters are provided as inputs to the neural network 154. Based on the 12 parameters, the neural network 154 estimates the location and orientation of the magnet 120. The neural network 154 is then provided with data indicating the actual location and orientation of the magnet 120. This process is repeated a large number of times such that the neural network 160 "learns" to accurately estimate the location and orientation of the magnet 120 based on the 12 parameters. In the present case, the learning process described above (e.g., providing 12 parameters, estimating the location, and providing the actual location) was repeated 1,000 times. The neural network 154 learns the best estimated position for a set of 12 parameters. It should be noted that the user of the detector system 100 need not operate the neural network 154 in the learn mode. Rather, data from the learn mode process is provided along with the detector system 100. In normal operation, the neural network 154 is utilized only in the operational mode.

In the operational mode, the 12 parameters from the magnetic sensors 108–114 are given to the neural network 154, which generates an initial estimate of the location and orientation of the magnet 120. Based on experiments performed by the inventors, the neural network 154 can provide an initial estimate of the location of the magnet 120 within approximately ±2 cm. Such an accurate initial estimate reduces the number of iterations required by the estimation processor 152 to accurately determine the location a of the magnet 120. It should be noted that if the location a of the magnet 120 is sufficiently far from the detector system 100, the magnetic sensors 108–114 will provide very low signal levels. Accordingly, the neural network 154 will not generate an initial estimate until the parameters (i.e., the 12 input signals from the magnetic sensors 108–114) are above a minimum threshold and can therefore provide a reliable signal.

Given an accurate initial estimate, the estimation processor 152 can perform the iteration process described above and determine the location a of the magnet 120 within ±1 mm. Clinical studies performed using the detector system 100 have demonstrated the satisfactory operation of the detector system 100. Those clinical studies are described below.

The detector system 100 also includes a display interface 156, shown in FIG. 5A, to permit the magnet image to be displayed on an external display (not shown). As those skilled in the art will appreciate, many of the components of the detector system 100, such as the CPU 146 and the memory 148 are conventional computer components. Similarly, the display interface 156 may be a conventional interface that allows the detector system image to be shown on a PC display or other monitor, such as a live image monitor 168 (see FIG. 5B).

One advantage of an external display is that the housing 102 may remain in a fixed position with respect to the patient. In this embodiment, the four magnetic sensors 108–114 may be replaced with a large number of sensors (e.g. sixteen sensors) uniformly distributed throughout the housing 102 to form an array of magnetic sensors. As the magnet 120 is moved relative to the housing 102, the movement is detected by three or more of the magnetic sensors and the position of the magnet calculated and shown on the external display. In this embodiment, the user need not reposition the housing, but simply views the external display where the array of magnetic sensors can track the position of the magnet 120.

Figure 5B:
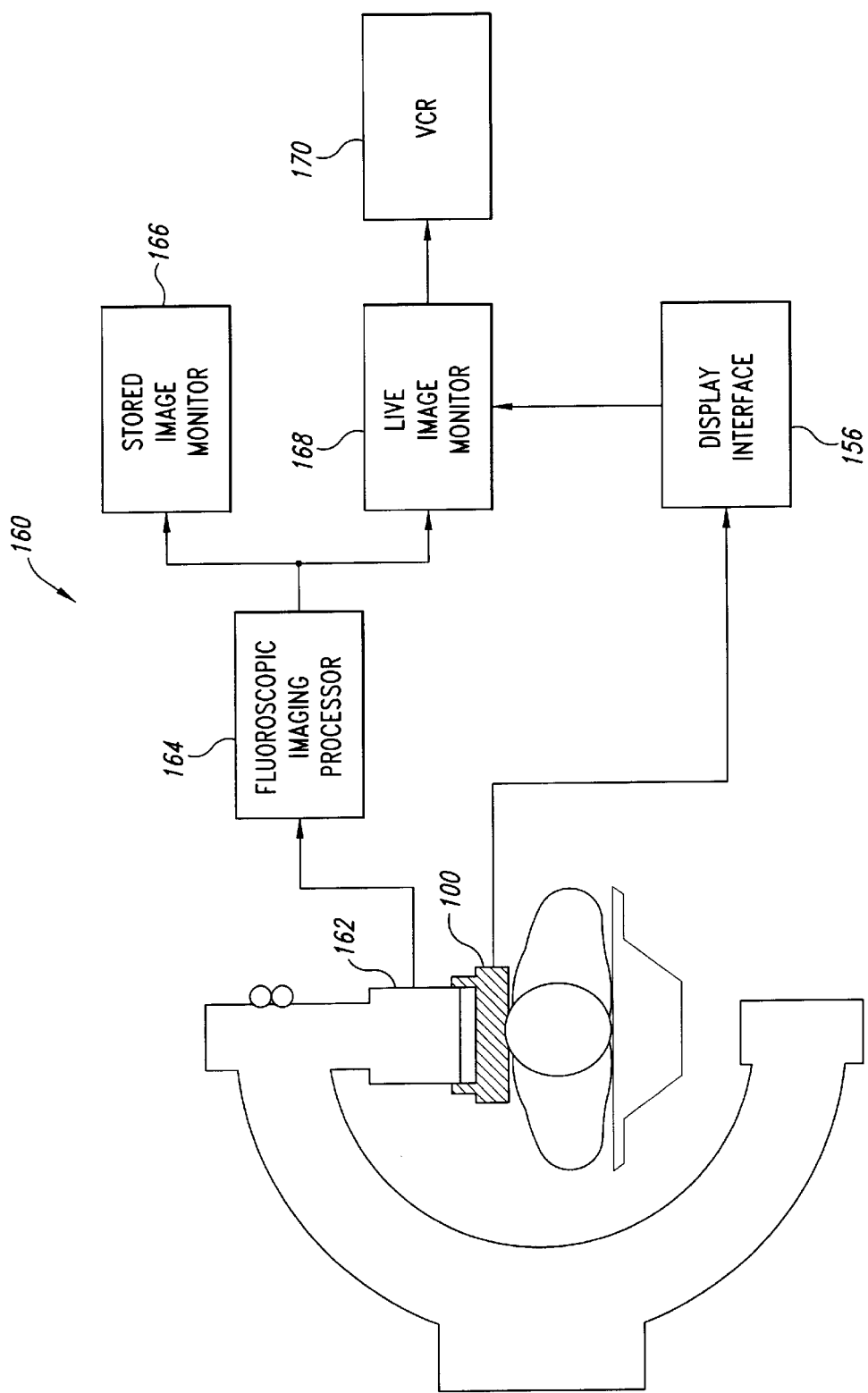
FIG. 5B is a functional block diagram illustrating the operation of the system of FIG. 5A to display the location of a magnet in conjunction with a conventional imaging system.

Another advantage of an external video display is the ability to combine the image generated by the detector system 100 with image data generated by conventional techniques. For example, FIG. 5B illustrates the operation of the detector system 100 in conjunction with a fluoroscope system 160. The fluoroscope system 160 is a conventional system that includes a fluoroscopic head 162, a fluoroscopic image processor 164, and an image storage system that includes a stored image monitor 166 and the live image monitor 168. In addition, a conventional video cassette recorder 170 can record the images generated by the fluoroscope system 160 and images generated by the detector system 100. The operation of the fluoroscope system 160 is known in the art, and will not be described in greater detail herein.

The detector system 100 is fixedly attached to the fluoroscopic head 162 in a known spatial relationship. A single "snapshot" image of the patient can be obtained using the fluoroscopic system 160 and displayed, by way of example, on the live image monitor 168. As a catheter containing the magnet 120 (see FIG. 4) is inserted in the patient, the detector system 100 detects the location a of the magnet 120 in the manner described above and can project the image of the magnet on the live image monitor 168 along with the snapshot image of the patient. In this manner, the user may advantageously utilize the snapshot fluoroscope image provided by the fluoroscope system 160 combined with the live image data provided by the detector system 100.

For satisfactory operation of this aspect of the invention, it is necessary to have proper alignment between the fluoroscope system 160 and the detector system 100. This alignment, or "registration" may be accomplished by placing a radio-opaque marker on the chest of the patient where the radio-opaque marker is aligned with the corners of the detector system 100. When the fluoroscope system 160 generates the snapshot image, the corners of the detector system 100 are indicated on the live image monitor 168 by virtue of the radio-opaque markers. The advantage of the image overlay using the detector system 100 is that the patient is only momentarily exposed to radiation from the fluoroscope system 160. Thereafter, the snapshot image is displayed with data from the detector system 100 overlaid on top of the snapshot image. Although this process has been described with respect to the fluoroscope system 160, those skilled in the art can appreciate that the present invention is applicable to any image-guided surgical process using X-ray, magnetic resonance imaging (MRI), positron emission tomography (PET), and the like.

The Earth's magnetic field is also detected by the magnetic sensors 108–114. However, assuming the Earth's magnetic field to be constant across the housing 102, the contribution of the Earth's magnetic field to the readings from the magnetic sensors 108–114 will be the same. By generating a differential signal between any two of the magnetic sensors 108–114, the effects of the Earth's magnetic field may be effectively canceled. However, as discussed above, there may be perturbations or inhomogeneity in the Earth's magnetic field caused by metallic elements, such as equipment, hospital bed rails, metal building structural elements, and the like. Because of the unpredictable nature of such interfering elements, proper operation of the detector system 100 requires calibration. The detector system 100 may be readily calibrated to compensate for localized perturbations in the Earth's magnetic field using a calibration processor 158, shown in FIG. 5A. It should be noted that the calibration processor 158 is preferably implemented by computer instructions stored in the memory 148 and executed by the CPU 146. However, for the sake of clarity, the functional block diagram of FIG. 5A illustrates the calibration processor 158 as an independent block since it performs an independent function. Alternatively, the calibration processor 158 can be implemented by other conventional computer components, such as a digital signal processor (not shown).

An initial calibration is performed before the magnet 120 is introduced into the patient. Thus, initial calibration occurs outside the presence of the magnetic field generated by the magnet 120. A measurement is performed using the detector system 100. Under ideal conditions, with no localized perturbations in the Earth's magnetic field, the signals generated by the magnetic sensors 108–114 will be the same. That is, each of the sensing elements oriented in the x direction will have identical readings, while each of the sensing elements oriented in the y direction will have identical readings and each of the elements oriented in the z direction will have identical readings. However, under normal operating conditions, localized perturbations in the Earth's magnetic field will exist. Under these circumstances, the signals generated by each sensor element of the magnetic sensors 108–114 all have some different value based on the detection of the Earth's magnetic field. The readings of any two of the magnetic sensors 108–114 may be differentially combined which, theoretically, will cancel out the Earth's magnetic field. However, due to localized perturbations in the Earth's magnetic field, there may be an offset value associated with the reading.

The calibration processor 158 determines the offset values associated with each of the magnetic sensors and compensates for the offset values during the measurement cycle. That is, the offset value for each of the magnetic sensors 108–114 is subtracted from the reading generated by the ADC 142 (see FIG. 5A). Thus, the differential reading between any two of the magnetic sensors 108–114 will be zero before the magnet 120 is introduced. Thereafter, as the magnet 120 is introduced, the differential readings from the magnetic sensors 108–114 will have nonzero values due to the static magnetic field generated by the magnet 120. If the detector system 100 is stationary, as illustrated in FIG. 5B, a single calibration process is sufficient to cancel out the effects of the Earth's magnetic field, including localized perturbations caused by external objects, such as metallic equipment, building structural elements, and the like.

Figure 5C:
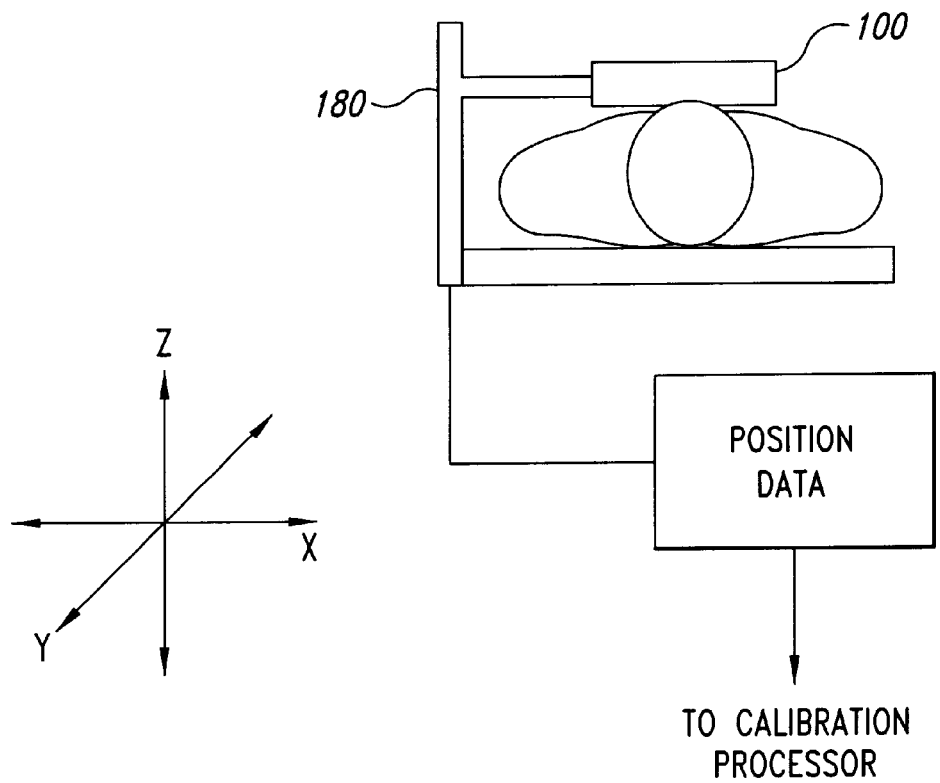
FIG. 5C illustrates an embodiment of the system of FIG. 5A to monitor the location of the detector system.

However, in certain embodiments, it is desirable to move the detector system 100 over the surface of the patient. As the detector system 100 is moved to a new position on the patient, the localized perturbations in the Earth's magnetic field may cause a degradation in the accuracy of the detector system 100 since the effects of the localized perturbations may no longer be completely canceled. However, the calibration processor 158 allows a continuous automatic recalibration of the detector system 100, even in the presence of the magnet 120. This is illustrated in FIG. 5C, where the detector system 100 is fixedly attached to a digitizing arm 180. The digitizing arm 180 is a conventional component that allows three-dimensional movement. The digitizing arm 180 may be conveniently attached to the patient bedside. In a preferred embodiment, the detector system 100 is attached to the digitizing arm and oriented such that the three dimensions of movement of the digitizing arm correspond to the x axis, y axis, and z axis, respectively, of the detector system 100. As the user moves the detector system 100, the digitizing arm accurately tracks the position of the detector system and generates data indicative of the position. The detector system 100 utilizes this position data to calculate the change in the measured magnetic field caused by the magnet 120 as the detector system 100 is moved. In this manner, the localized effects of the magnet 120 may be removed, with the resultant measurement being indicative of the localized perturbations of the Earth's magnetic field at the new position of the detector system 100.

The automatic recalibration process is particularly useful in a situation, such as a peripherally inserted central catheter (PICC), which may typically be inserted in the patient's arm and threaded through the venous system into the heart. Using conventional technology, the surgeon would typically place marks on the chest of the patient to mark the expected route over which the catheter will be inserted. Without the present invention, the surgeon must blindly insert the catheter and verify its location using, by way of example, fluoroscopy. However, the detector system 100 permits the surgeon to track the placement of the PICC.

In the example above, the detector system 100 may be located over the arm of the patient where the PICC will be initially inserted. Following the initial calibration (in the absence of the magnet 120) the detector system 100 is calibrated and will compensate for the effects of the Earth's magnetic field including any localized perturbations. When the magnet 120 is introduced, the detector system 100 detects and displays the location a of the magnet in the manner previously described. As the surgeon inserts the PICC (with the attached magnet 120), it may be desirable to relocate the detector system to thereby track the progress of the PICC. Using the digitizing arm 180, the surgeon relocates the detector system 100 to a new location. For example, assume that the detector system 100 is moved six inches in the y direction, three inches in the x direction, and has not moved in the z direction. Based on the new location of the detector system 100, and using the technology described above, the estimation processor 152 (see FIG. 5A) can calculate the magnetic field at the new location due to the magnet 120. Given the contribution to magnetic field at the new location that results from the magnet 120, it is possible to subtract out the effects of the magnet 120. In the absence of the magnetic field from the magnet 120, any remaining or "residual" magnetic field is assumed to be the result of the Earth's magnetic field. The residual reading is processed in the manner described above for an initial calibration to thereby rezero or recalibrate the detector system 100 to compensate for the Earth's magnetic field, including localized perturbations, at the new location. Following this recalibration process, a measurement cycle may be initiated with the resultant measurement of the magnetic field being due solely to the presence of the magnet 120.

The user may manually recalibrate the detector system 100 at any point in time. However, the advantage of the technique described above is that the detector system 100 may be automatically recalibrated on a continuous basis as the detector system 100 is used. The digitizing arm 180 provides a continuous reading of the position of the detector system 100 and thus makes it possible to accurately track the location of the detector system. As the detector system 100 moves, it is constantly recalibrated to recompensate for the Earth's magnetic field. In the example above, the detector system 100 may be moved at will to follow the movement of the PICC as it is inserted into the heart without concern that external influences, such as a hospital bed rail, will cause a degradation in the accuracy of the measurement. Although the recalibration system has been described above with respect to the digitizing arm 180, it can be appreciated that other position sensing systems may also be readily utilized.

For example, commercial tracking systems are manufactured by Ascension Technology and Polhemus. The system manufactured by Ascension Technology, known as the "Bird Tracker" comprises an array of sensors that measure six degrees of freedom and provide accurate measurements within one-half inch at a distance of five feet and provide rotational information within one-half degree at a distance of five feet. The sensing elements used in the Bird Tracker may be attached to the housing 102 and the position of the housing tracked using the commercial system. Similarly, the Polhemus device, known as the "3-D Tracker," provides similar location measurements without the need of the digitizing arm 180.

Figure 6A:
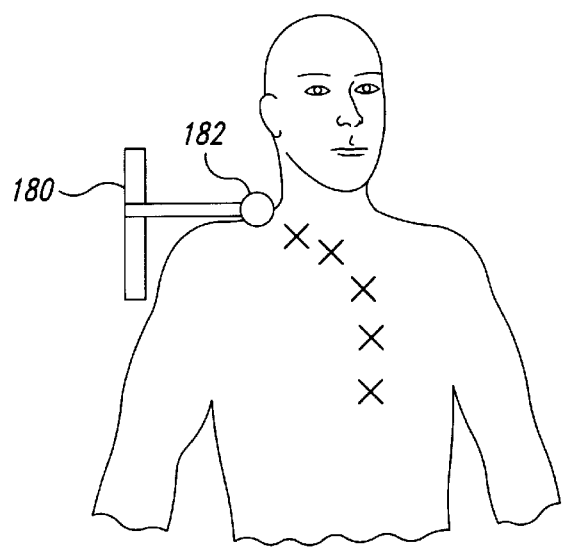
FIG. 6A illustrates the use of the sytsem of FIG. 5C to select landmark locations on a patient.
Figure 6B:
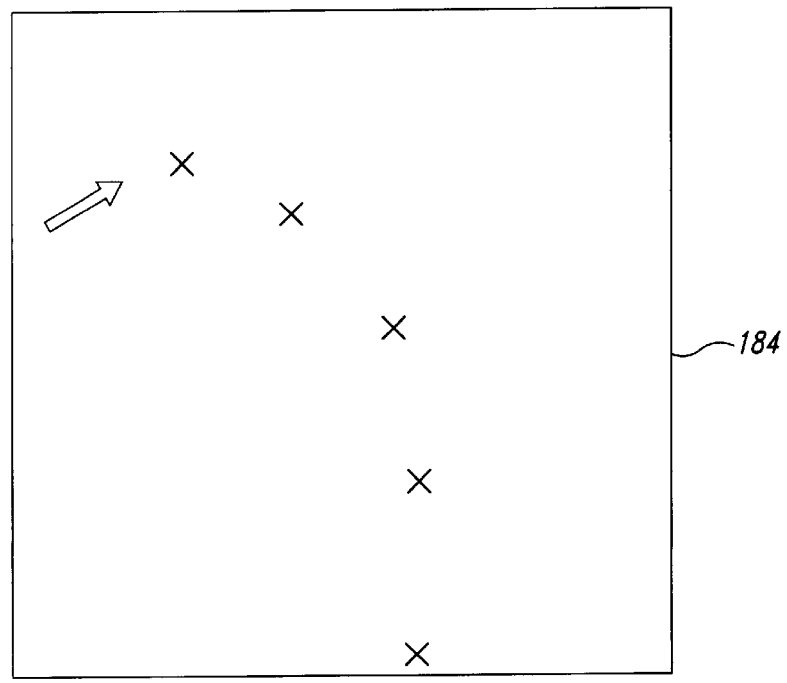
FIG. 6B illustrates the display of the selected locations and the location of a magnet.

Another application of position tracking, using, by way of example, the digitizing arm 180 permits the surgeon to provide digitized landmarks that will be shown on the display. A common surgical technique to assist in insertion of a catheter is to place landmarks on the surface of the patient that approximate the route that will be taken by the catheter. For example, with conventional technology the surgeon may place a series of x's on the patient's chest with a marker pen as landmarks to assist in insertion of electrical pacemaker leads. With the principles of the present invention, the digitizing arm 180 may be used to electronically record landmarks specified by the surgeon. This aspect of the invention is illustrated in FIG. 6A, when a computer input stylus 182 or other electronic input device is mounted to the digitizing arm 180. The computer stylus 182 may be attached to the detector system 100 or attached to the digitizing aim 180 in a position corresponding to, by way of example the center of the detector system. Prior to insertion of the catheter with the magnet 120, the surgeon may utilize the digitizing arm 180 and the computer stylus 182 to electronically generate landmarks, illustrated in FIG. 6A by a series of x's. It should be noted that the computer stylus 182 electronically "marks" the patient, but need not place any actual marks on the patient. In the example above, where heart pacemaking leads will be inserted, the surgeon may place a series of electronic landmarks from the neck to the heart along the route in which the pacemaker leads will be inserted. At each landmark, the digitizing arm 180 records the position marked by the surgeon. In subsequent operation, when the catheter with the magnet 120 is inserted into the patient, the digitizing arm 180 notes the location of the magnet 120 with respect to the landmarks previously marked by the surgeon. The landmarks are shown on an external display 184, shown in FIG. 6B, along with the position of the magnet 120, which is indicated by an arrow. As the surgeon inserts the magnet 120, the progress is shown on the external display 184 such that the magnet 120 passes along from landmark 1 to landmark 2 to landmark 3, and so forth. With this technique, the surgeon can readily detect divergence from the expected route. For example, if the catheter and magnet 120 are inadvertently diverted into a different vein, the surgeon will readily note the divergence from the marked pathway and quickly identify the problem. The catheter and magnet 120 may be withdrawn and reinserted to follow the landmarked pathway.

Figure 7A:
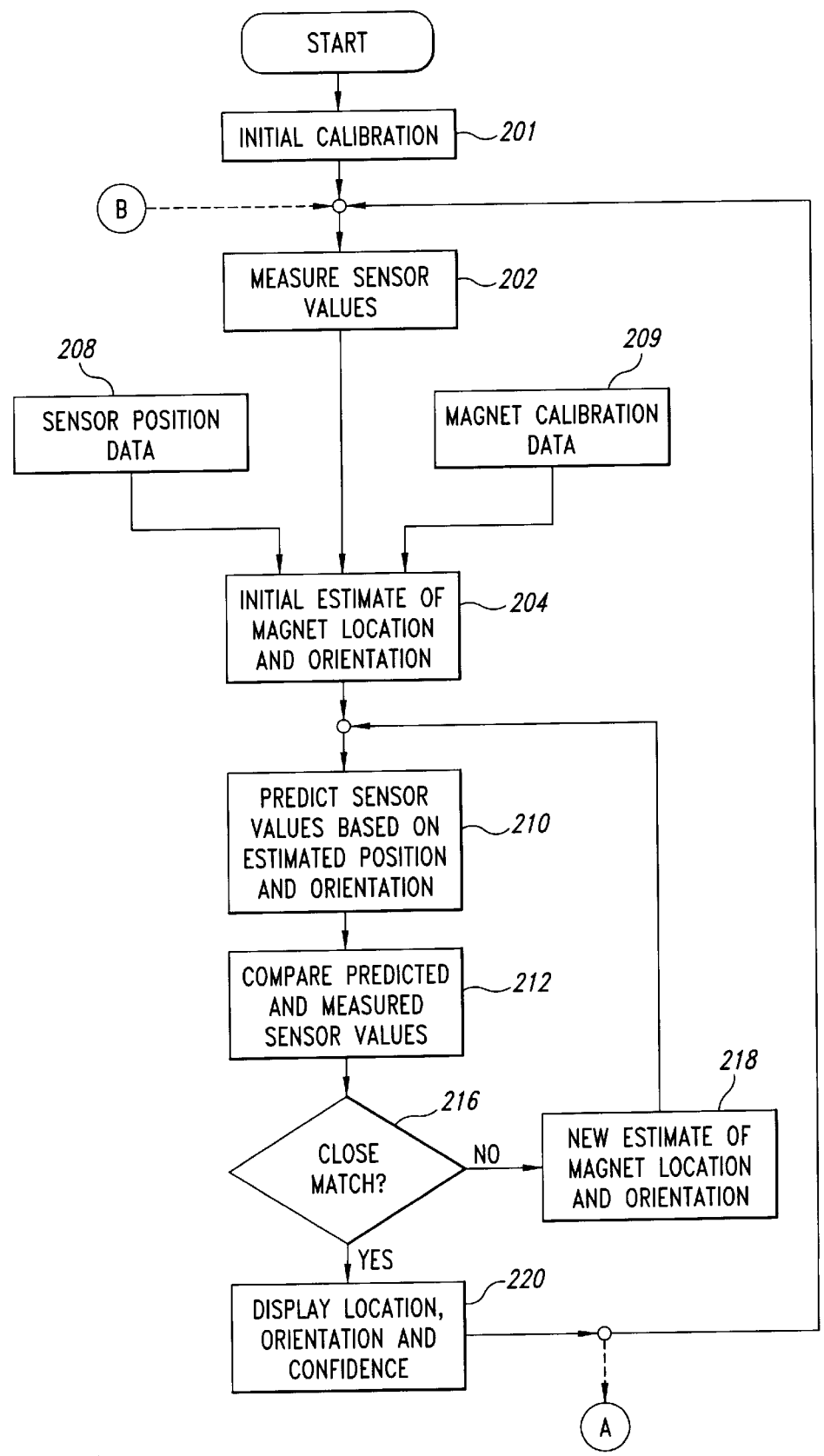
FIG. 7A is a flowchart used by the system of FIG. 5A to determine the location of a magnet.

The general operation of the detector system 100 is illustrated in the flowchart of FIG. 7A. At a start 200 the magnet 120 (see FIG. 4) has been inserted into the patient. In step 201, the system undergoes an initial calibration. In an exemplary embodiment, the initial calibration is performed before the magnet 120 is introduced. Thus, the system 100 compensates for the effects of the Earth's magnetic field, including localized perturbations, in the absence of any contribution from the magnet 120. Alternatively, the magnet 120 may be positioned in a known location with respect to the housing 102 such that the effects of the magnetic field caused by the magnet 120 are known and can be canceled in the manner described above with respect to the automatic recalibration process. That is, the contribution to the measured magnetic field caused by the magnet 120 in the known location can be subtracted from the measured readings with the resultant residual value being caused only by the Earth's magnetic field. Following the initial calibration, in step 202, the detector system 100 measures sensor values from the magnetic sensors 108–114. In step 204, the estimation processor 152 (see FIG. 5A) calculates an initial estimate of the location a and orientation of the magnet 120. The initial estimate includes sensor position data from step 208 and magnet calibration data from step 209. The sensor position data calculated in step 208 provides data relating the position of each of the magnetic sensors 108–114 relative to a selected origin. For example, one magnetic sensor (e.g., magnetic sensor 108) may be arbitrarily selected as the mathematical origin for purposes of determining the relative positions of the other magnetic sensors (e.g., magnetic sensors 110–114). The common origin provides a frame of reference for purposes of the mathematical calculations. As previously discussed, the magnetic sensors 108–114 are aligned with respect to the common origin so that each magnetic sensor measures the magnetic field in the same x, y, and z directions. As those of ordinary skill in the art can appreciate, any selected origin can be used satisfactorily with the detector system 100.

The magnetic calibration data derived in step 209 is typically provided by the magnet manufacturer and includes data related to the strength of the magnetic dipole m (see FIG. 4), as well as the size and shape of the magnet 120. The measured sensor values, sensor position data, and magnet calibration data are provided as inputs to the estimation processor 152 (see FIG. 5A) in step 204.

In an exemplary embodiment, the initial estimate of the location a is provided by the neural network 154 (see FIG. 5A) based on the measured sensor values derived in step 202. As previously discussed, the neural network 154 may require minimum values from the magnetic sensors 108–114 to assure a reliable initial estimate. The neural network 154 provides the initial estimate of magnet location and orientation.

In step 210, the estimation processor 152 (see FIG. 5A) calculates predicted sensor values. As described above, this requires a measurement $\Delta_{ij}$ (predicted) for each combination of the magnetic sensors 108–114 in each of the three orthogonal directions x, y, and z. In step 212, the estimation processor 152 compares the predicted sensor values (i.e., $\Delta_{ij}$ (predicted)) with the measured sensor values (i.e., $\Delta_{ij}$ (measured)). In decision 216, the estimation processor 152 determines whether the predicted and measured sensor values match within a desired degree of tolerance. If the predicted sensor values and the measured sensor values are not a close match, the result of decision 216 is NO. In that event, the estimation processor 152 calculates a new estimate of the magnet location a and orientation in step 218. Following the calculation of a new estimated location a of the magnet 120, the estimation processor 152 returns to step 210 to calculate a new set of predicted sensor values using the new estimate of magnet location and orientation. The estimation processor 152 continues this iterative process of adjusting the estimated location a of the magnet 120 and orientation and comparing predicted sensor values with measured sensor values until a close match is achieved. When a close match between the predicted sensor values and the measured sensor values is achieved, the result of decision 216 is YES. In that event, in step 220 the detector system 100 displays the magnet location a and orientation on the display 106 (see FIGS. 3A, 3B, and 4). In addition, the detector system 100 may display a confidence value indicative of a degree of confidence with which the location a and orientation of the magnet 120 have been determined. The calculation of a confidence value based on statistical data is well known in the art and need not be described in detail herein. Following the display of location and orientation data in step 220, the detector system 100 returns to step 202 and repeats the process on a new set of measured sensor values. If cost function is too high, a close match may not be achieved in decision 216. Such conditions may occur, for example, in the presence of extraneous magnetic fields. In practice, it has been determined that close matches have a cost function in the range of 1–2 while the minimum cost function for an inaccurate local minimal are orders of magnitude greater. If a close match cannot be achieved (i.e., the cost function is too great), the detector system 100 can start the measurement process anew with a new estimated location or generate an error message indicating an unacceptably high cost function.

Figure 7B:
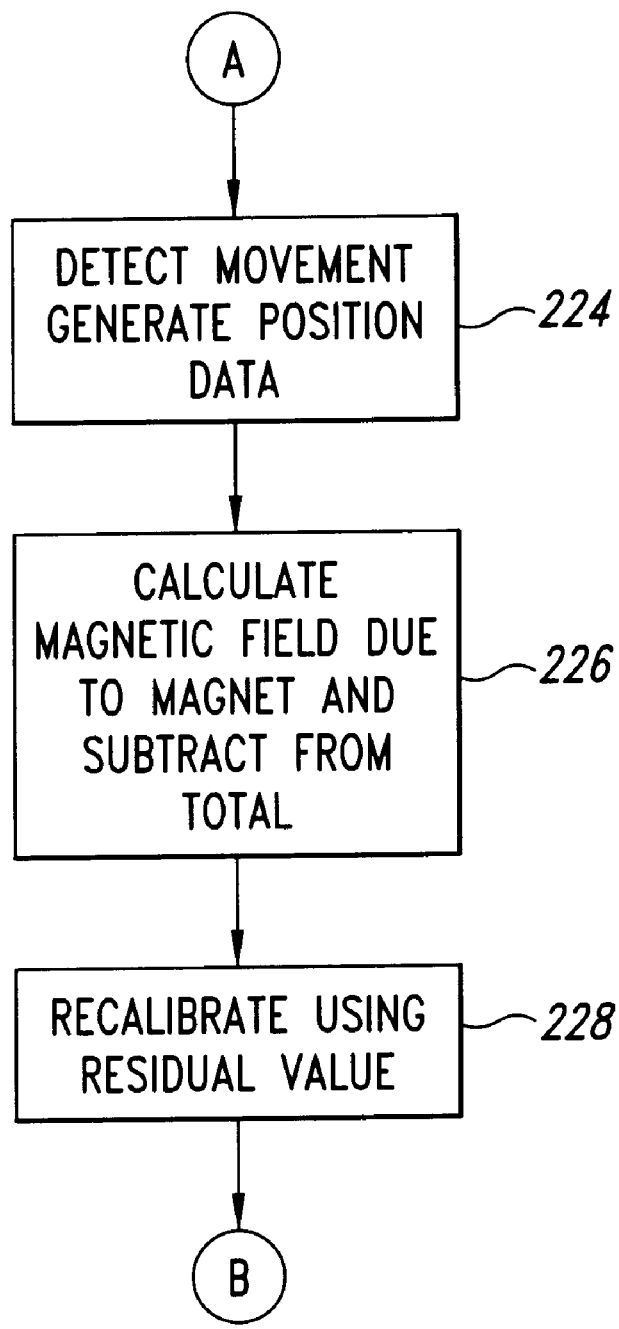
FIG. 7B is a flowchart illustrating the automatic calibration function of the system of FIG. 5A.

The flowchart of FIG. 7B illustrates the steps performed by the calibration processor 158 if automatic recalibration is implemented within the detector system 100. In this implementation, following the completion of step 220, the system 100 may optionally move to step 224, illustrated in FIG. 7B, wherein the calibration processor 158 obtains the position data from the digitizing arm 180 (see FIG. 5C) indicating the present location of the detector system 100. Given the new location of the detector system 100 and the known location a of the magnet 120, the calibration processor 158 calculates the magnetic field resulting from the magnet and subtracts the effects of the magnet from the current measurements in step 226. As a result of this process, the remaining residual values measured by the magnetic sensors 108–114 (see FIG. 5A) are due to the effects of the Earth's magnetic field, including localized perturbations.

In step 228, this residual value is used to rezero the detector system 100 to compensate for the effects of the Earth's magnetic field at the new location. Following the recalibration process, the detector system 100 returns to step 202, shown in FIG. 7A, to perform additional measurement cycles with the detector system 100 at the new location and recalibrated for operation at the new location.

It should be noted that the automatic recalibration process illustrated in the flowchart of FIG. 7A automatically and continuously recalibrates the detector system 100. However, in an alternative embodiment, the calibration processor 158 will perform the recalibration process only if the detector system 100 has been moved by a predetermined amount. This prevents the unnecessary recalibration when the detector system 100 has not been moved.

The iterative estimation process is described above using the difference in magnetic strength B provided by different pairs of magnetic sensors 108–114. Alternatively, the detector system 100 can use the measured field gradient values G. In this embodiment, equation (2) may be fit to the measured values, in a manner as described above with respect to the iterative process to fit the measurements of B. With respect to the flowchart of FIG. 7A, the step 202 provides gradient values with respect to pairs of the magnetic sensors 108–114. For example, a magnetic gradient measurement can be calculated using the magnetic field B measured by the magnetic sensor 114 with respect to the magnetic field measured by each of the remaining magnetic sensors 108–112, respectively. In step 204, the estimation processor 152 determines an initial estimate of the magnet location and orientation, and, in step 210, calculates predicted sensor values using equation (2). In step 212, the measured sensor values are compared with the predicted sensor values using conventional techniques, such as the cost functions described above. The iterative process continues until the measured sensor values and the predicted sensor values match within the predetermined degree of tolerance.

In yet another alternative technique, the detector system 100 utilizes the measurement data and solves equation (2) for a directly. The direct solution approach utilizes the fact that G is a symmetric matrix with positive eigenvalues. The eigenvalues and eigenvectors of the matrix G may be calculated and used algebraically to solve for the location a and m directly. This assumes that the magnitude, but not the direction, of m is known. In practice, the magnitude m is known because magnet calibration data is provided by the manufacturer. It should be noted that this technique requires an additional magnetic sensor to determine the orientation of the magnetic dipole. Mathematically, the orientation of the magnetic dipole is indicated by a + or – sign. The additional magnetic sensor, which need only measure the magnetic field strength B, is used to determine the sign of the mathematical function. In addition, combinations of these various techniques may be used by the detector system 100 to determine the location a of the magnet 120.

In yet another alternative, a Kalman filter may be used with equations (1) and (2) above to track the position of the magnetic dipole m with respect to the multi-detector array formed by the magnetic sensors 108–114. As is known to those of ordinary skill in the art, Kalman filters are statistical predictive filters that use statistical signal processing and optimal estimation. Numerous textbooks, such as "Tracking And Data Association," by Y. Bar-Shalom and R. E. Fortmann, Academic Press, Boston, 1988, provide details on the theory and operation of Kalman filters. In addition to the individual techniques described above, it is possible to use any or all of these techniques in a combination, such as a sum of cost functions for each sensor type. For example, the differences between $\Delta_{ij}$ (predicted) and $\Delta_{ij}$ (measured) can be required to match within a certain tolerance. If the multiple mathematical techniques are unable to identify a solution for which all difference values meet that tolerance, then an error can be signaled to the operator using the display 106 (see FIG. 5A). Assuming the errors in each sensor measurement are independent and small, the uncertainty in the estimate of the location a can be calculated using, for example, Cramer-Rao bounds. Thus, a degree of redundancy between measurement techniques can be advantageously implemented by the detector system 100. Such redundancy is highly desirable for biomedical applications.

FIG. 3 illustrates the operation of the detector system 100 for a specific configuration of the magnetic sensors 108–114. However, the techniques described above may be generalized to virtually any fixed configuration of sensors. A minimum of one gradient sensor or eight magnetic field sensors is required to measure G(s) and B(s), respectively, assuming that the strength of the magnetic dipole m is known. The magnetic sensors can be configured relatively arbitrarily and thus may be readily positioned at locations within the housing 102 (see FIGS. 3A and 3B) based on instrument design and/or other signal or noise considerations.

The magnetic sensors 108–114 may be calibrated using the known strength of the Earth's magnetic field. In the absence of any inhomogeneous fields (i.e., away from any strong magnetic dipoles) the X sensor element of all sensors 108–114 can be read at the same time. Similarly, all Y sensor elements and Z sensor elements can be read at the same time. In any configuration, the sum of the squares of the average readings of the magnetic field strength for each orthogonal direction (i.e., $B_x$, $B_y$, and $B_z$) should be constant. The constant value of the Earth's magnetic field can be used to determine the appropriate calibration factors for each magnetic sensor using conventional algebraic and least squares fitting methods.

An alternative calibration technique uses a small magnet of known strength placed in one or more locations relative to the magnetic sensors 108–114. Measurements are performed at each of the one or more locations to determine the appropriate calibration factors for each magnetic sensor. Other techniques, such as the use of an electromagnetic cage, Helmholtz cage, or the like, may also be used to calibrate the magnetic sensors 108–114.

The display 106 (see FIG. 3) provides graphical display of the position of the magnet 120 with respect to the housing 102. FIGS. 8A to 8D illustrate some of the different techniques used by the detector system 100 to indicate the location a of the magnet 120 (see FIG. 4). In the embodiment illustrated in FIG. 8A, the display 106 uses a circle 250 and a pair of orthogonal lines 252a and 252b to indicate the location a of the magnet 120 relative to the housing 102. The orthogonal lines 252a and 252b provide a visual indicator to the caregiver to assist in determining when the magnet 120 is centered under the detector system 100.

Figure 8A:
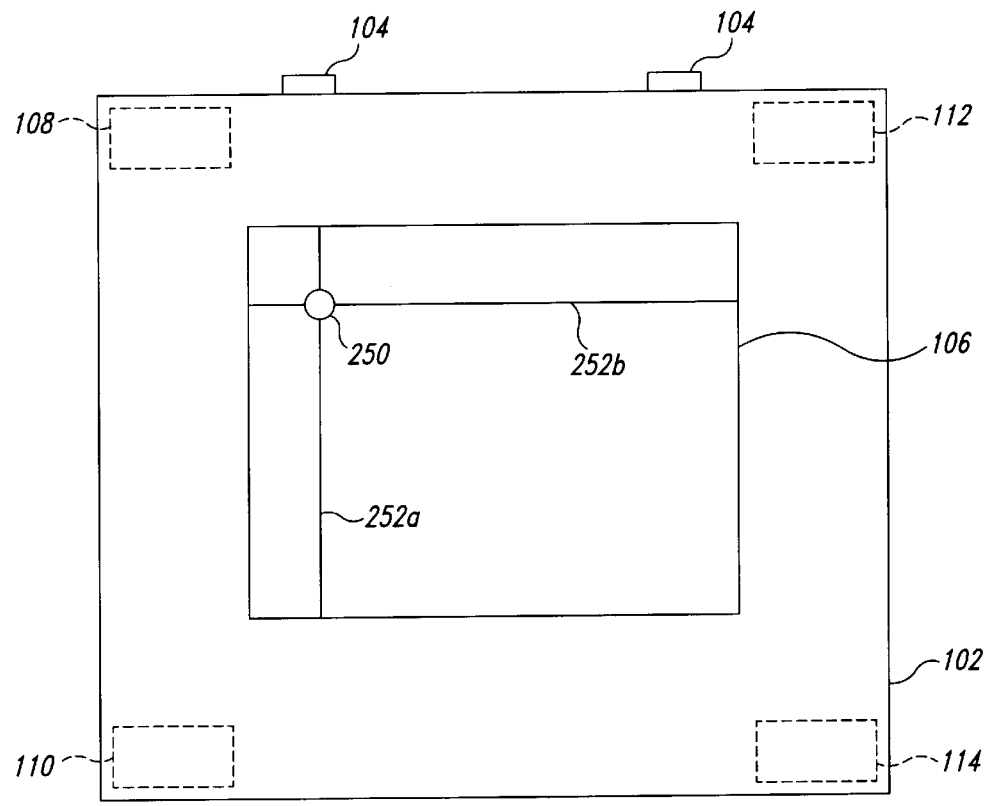
FIG. 8A illustrates one embodiment of the visual display used by the detector of FIG. 3.
Figure 8B:
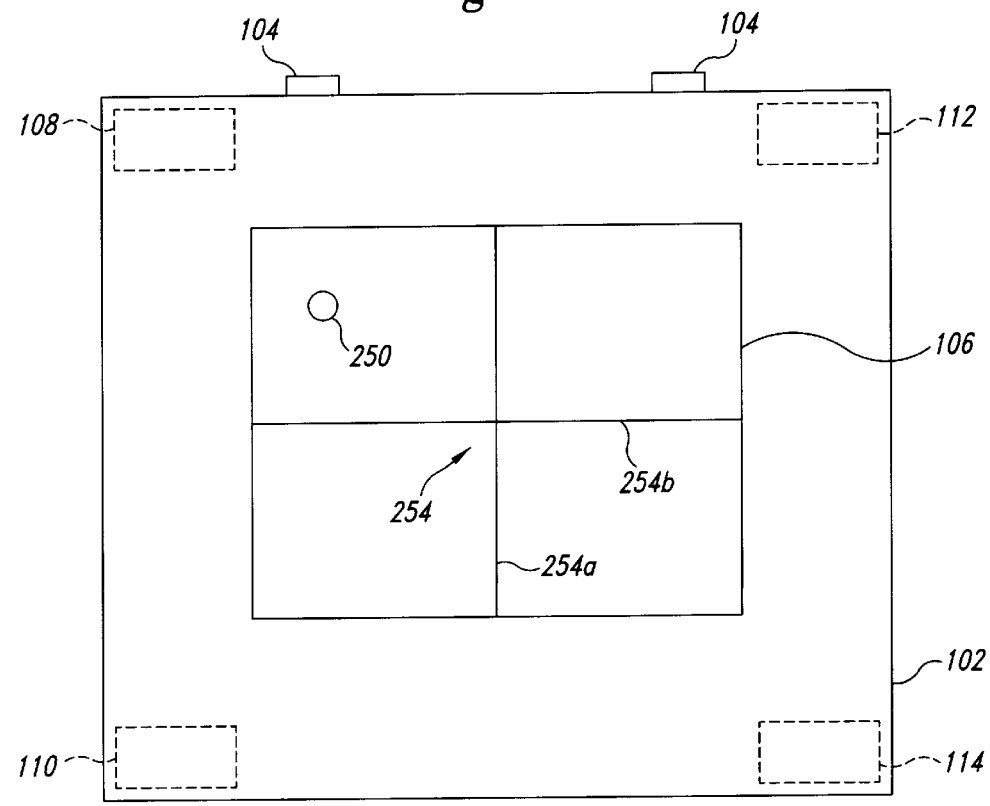
FIG. 8B is an alternative embodiment of the indicator used with the detector of FIG. 3.

In an alternative embodiment, illustrated in FIG. 8B, a fixed indicator 254, such as orthogonal lines 254a and 254b, form cross-hairs over the center of the display 106. The circle 250, or other indicator, is used to provide a visual indication of the location a of the magnet 120 relative to the housing 102. The circle 250 is centered in the cross-hairs in the center of the display 106 when the magnet 120 is centered directly beneath the detector system 100.

Figure 8C:
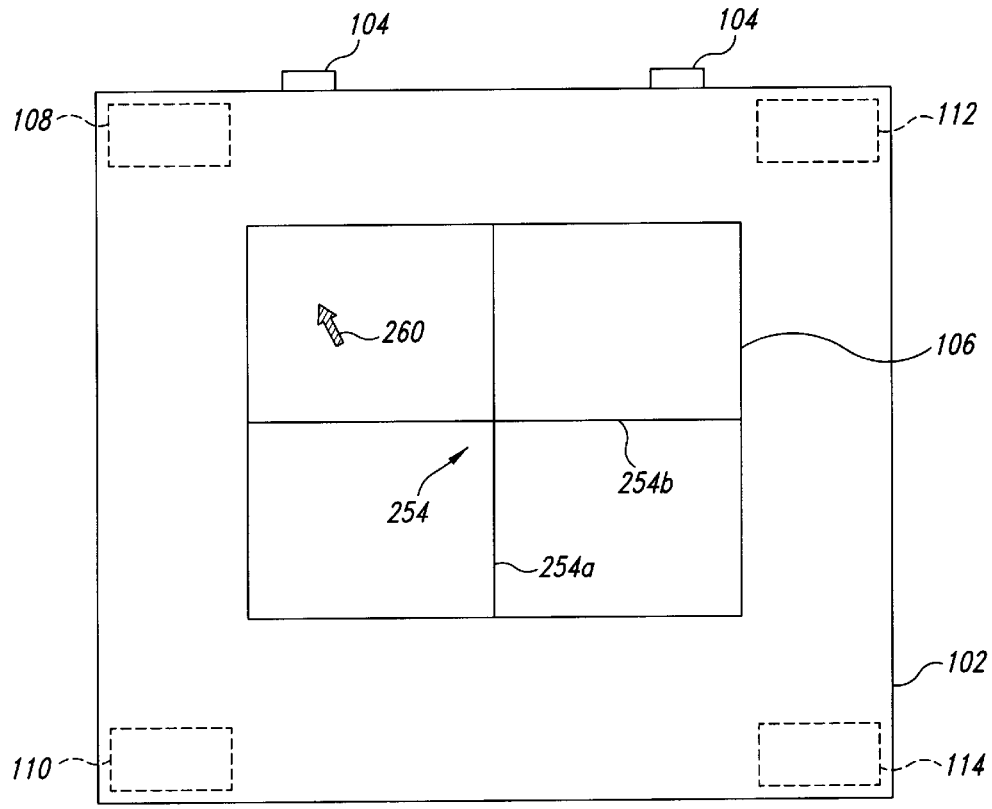
FIG. 8C is yet another alternative embodiment of the display used with the detector of FIG. 3.

In yet another embodiment, shown in FIG. 8C, the display 106 provides a different indicator, such as an arrow 260, to provide a visual indication of the location a of the magnet 120. The arrow 260 may also be used to indicate the orientation of the magnet 120.

Figure 8D:
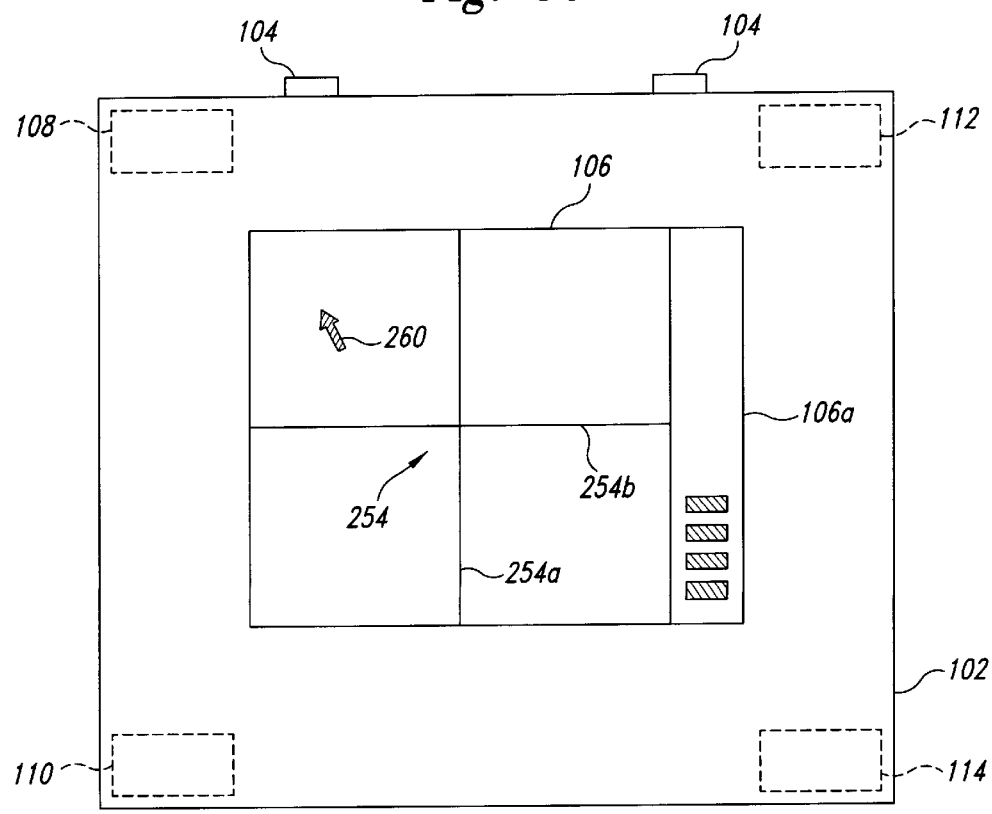
FIG. 8D is yet another alternative embodiment of the display of the detector of FIG. 3 with a depth indicator indicating the distance of the magnet from the detector.

The depth of the magnet 120 beneath the surface of the patient can be indicated on the display 106 in a variety of fashions. For example, a portion 106a of the display 106 can provide a visual indication of the depth of the magnet 120 using a bar graph, such as illustrated in FIG. 8D. However, the depth indicator portion 106a of the display 106 can also provide a numerical read-out of the depth of the magnet 106 in absolute units, such as centimeters, or in relative units.

Thus, the detector system 100 determines the location a of the magnet 120 in a three-dimensional space and provides an easy-to-read visual indication of the location of the magnet, including a depth indication, as well as the orientation of the magnetic dipole. While the housing 102 is illustrated as a rectangular housing, with the magnetic sensors 108–114 distributed equidistantly within the housing 102, the rectangular shape was chosen for its ease in grasping by the caregiver. However, the housing 102 can have any shape or size. Furthermore, the display 106, while illustrated as a liquid crystal display, can be any convenient two-dimensional display, such as a dot matrix display or the like. Thus, the present invention is not limited by the specific size or shape of the housing 102 or by the specific type of display 102. In addition, the detector system 100 can operate satisfactorily with a variety of different magnetic sensors. Thus, the present invention is not limited by the specific number or type of magnetic sensors employed in the detector system 100.

Clinical Studies

The operation of the detector system 100 has been described for the detection of a static magnetic field associated with the magnet 120 inserted within a patient. The reliability of the detector system 100 has been tested in clinical studies, the results of which are described below. As will be described in detail below, the location of the magnet was determined using the detector system 100 and subsequently verified using conventional fluoroscopic measurements. Although initial results of the clinical studies indicate a relatively high error in the location detected by the measurement system 100, these errors are believed caused by inaccurate alignment of the detector system and the fluoroscopic measurement system. Thus, the errors are due to the misalignment rather than inherent inaccuracies in the detector system 100. In addition, revisions in the signal processing software resulted in greater reliability in later measurements in the clinical study, as discussed below.

One application of the detector system 100 is for the insertion of a catheter into the heart. Positioning a peripherally inserted central catheter (PICC) in the lower half of the superior vena cava, just above the right atrium, is a critical application for the detector system 100. Currently, practitioners perform this task "blindly" by measuring external anatomical landmarks and inserting the catheter to the measured depth. The success or failure of the insertion is unknown until a chest radiograph is obtained, which may not occur for several days. The detector system 100 was evaluated in an animal model as a possible solution to the "blind" placement.

Forty-four localizations were performed using the detector system to test its accuracy compared with conventional fluoroscopy. The detector system 100 located magnetic tagged PICCs to within an average of 0.4 cm, and a range of 0.2 cm to 1.25 cm. The detector system 100 also provided valuable real-time information about the path and orientation of the PICC tip during difficult insertions. The detector system 100 has demonstrated its ability to accurately locate a magnet tagged PICC relative to an external landmark and thus aid in catheter insertion. The measurement capabilities provided by the detector system 100 have the potential to improve clinical outcomes and thus reduce healthcare cost by decreasing catheter related problems in infusion therapy and by decreasing or eliminating the need for radiographic verification of PICC placements or other medical device placements.

Introduction

The PICC catheter is inserted to a peripheral vein in the patients arm and threaded into the superior vena cava to a point approximately 2 cm above the right atrium. The current method for introducing PICCs is to measure the distance from the point of insertion to the right sternal third intercostal space on the patient's chest and inserting the PICC to a depth equal to this measurement. The catheters are used for patients who require long-term (two weeks to six months) intravenous access for infusions, blood sampling, or blood transfusion. Currently, PICCs may be placed in outpatient or home settings by nurses, but the catheter cannot be used for infusions or sampling until its locations have been verified by radiography, which is inconvenient, relatively expensive, and can delay therapy for days.

Animal Model

Domestic cross-breed swine were used as the animal model for this study. Swine are an accepted model of the human cardiovascular system, and they have a cephalic vein in their thoracic limb that offers an acceptable route to the cranial vena cava, which is analogous to the superior vena cava in humans. A necropsy study done prior to the present study has indicated that the right sternal second intercostal space is a good external landmark for locating a point 2 cm above the right atrium in the cranial vena cava. The study also demonstrated that the chest wall to dorsal cranial vena cava distance ranges from 8.5 cm to 10 cm in animals weighing approximately 30 kg. This distance is analogous to the distance in humans for the analogous procedure. This last factor is significant, as the detector system 100 has a distance limit of approximately ten centimeters for locating the smallest magnetically tagged catheter used in the study.

Magnet Tagged PICCs

Commercially available PICC catheters and introducers were modified by placing one or more small cylindrical (NdFeB) magnets in the catheter tips and sealing the ends of the catheters with a non-sterile, medical grade silicone adhesive. Two catheter sizes were used. The smaller size catheters (4 Fr, 65 cm length) contained three N-40, Ni-plated 0.8 mm×2.5 mm magnets, and to the large catheters (5 Fr, 65 cm length) contained two N-40, Ni-plated 1.0 mm×2.5 mm magnets. The magnetic field strength of each magnetic tipped catheter was 3,129 milliGauss per cubic $cm^3$.

Magnet Field Detector

Two different versions of the detector system 100 were used in the study. A bench-top feasibility system was used for 44 localizations, and a hand-held prototype was used for 28 localizations. The hand-held unit included four magnetic field sensors (e.g, the magnetic sensors 108–114) mounted in a plastic case with control buttons and their associated electronics. A peripheral unit, containing processing hardware, software, and a power supply were also used with the hand-held version of the detector system 100. A single hand-held unit with three different software systems was used. Eight localizations were performed with revision 5.0 of the software, 16 localizations were performed with revision 5.1 of the software, and four localizations were performed with revision 5.2 of the software. As will be discussed below, the early revisions of the software for the hand-held prototype required significant software debugging and calibration. More reliable measurements were obtained with revision 5.2 of the software.

The bench-top version of the detector system 100 comprises four magnetic field sensors (e.g., the magnetic sensors 108–114) mounted on a Plexiglas platform with their associated electronics. The bench-top version of the detector system 100 was coupled to a personal computer (PC) where software was used to calculate the position and orientation of the magnet in three dimensions and to display the information on a conventional PC monitor in the form of an image indicating the magnet tipped catheter. Matching grids were placed on the Plexiglas platform and on the PC monitor to correlate the position on the monitor with the position on the external anatomy of the subject.

Clinical Procedure

The study was performed on nine healthy, approximately 25 kg domestic cross-breed swine. Each subject was fully anesthetized prior to the procedure and euthanized immediately following the procedure. After the initiation of the anesthesia, each subject underwent four sequential catheterizations. The subjects were measured externally from the point of insertion to the desired external landmark after venous access was established by a cut down in the axilla. One 4 Fr magnet PICC was inserted twice via an introducer in the right cephalic vein, and one 5 Fr magnet tagged PICC was inserted twice via an introducer in the left cephalic vein. Each catheter was placed in mid-clavicular and cranial vena caval locations and the position of the magnetic tagged tip was determined by one model of the detector system 100 in each location, resulting in the total of eight localizations per animal.

The location of the catheters was confirmed with fluoroscopy, and approximate accuracy of the detector system/fluoroscopic location correlation was determined by aligning the fluoroscope with the detector system 100 using a jig attached to the fluoroscope. Both versions of the detector system 100 were positioned over the subject prior to catheter insertion with a reticulated arm and leveled to within one degree relative to the fluoroscope jig using a conventional digital level. In the bench-top version of the detector system 100, an alignment rod was placed through the center of the jig and aligned over the grid on the Plexiglas platform that corresponds to the grid on the PC monitor. In the hand-held prototype version of the detector system 100, a paper marker was placed over the rendering on the screen and the alignment rod aligned with the paper marker.

Electronically captured fluoroscope images were analyzed with a commercial drawing program to estimate the measured error from the position determined by the detector system 100 and the center of the magnet mass as determined by fluoroscopy. This measurement is considered a conservative estimation. The image of the magnet tip was used as a reference to determine the scale of the image, and the tip may have been angled during the studies. An angled tip scales the image to a greater than actual magnification, thus increasing the measured error. This effect is believed to be minor as the magnet tips appeared to be relatively flat in each fluoroscopic image. Subjective estimates of the catheter position were made by the surgeon performing the measurements.

Results

The bench-top version of the detector system 100 functioned well during all localizations, but the first twelve insertions were complicated by difficulty in aligning the fluoroscope jig to the detector system 100. In the first twelve insertions, it was assumed that the alignment rod used to align the jig was straight, but it was shown that the alignment rod could be held at an angle, which affected the measured error of the localization. After the twelfth insertion, the alignment rod arrangement was altered to allow it to hang straight, and, after the sixteenth insertion, a hollow Plexiglas cylinder was added to the jig platform to keep the alignment rod straight. Following these modifications, the detector system 100 provided more consistent and accurate results.

The magnet tagged PICCs were inserted with ease into the swine cranial vena cavas through the introducers provided in the insertion kits accompanying the PICCs. The detector system 100 aided investigators twice during difficult PICC insertions. In one case, the detector system 100 had indicated that the catheter had doubled back on itself in the cranial vena cava, and the catheter was withdrawn until the image indicated the orientation was correct, and the catheter was properly inserted. In a second case, it was difficult to pass the PICC from the left cephalic vein into the external jugular vein due to a sharp angle at this junction, which was subsequently verified using fluoroscopy. The surgeon used the real-time feedback from the detector system 100 to twist, insert, and withdraw the catheter until it was clear that the catheter was oriented in an anatomically appropriate direction. When the catheter tip was past the sharp angle, it was inserted with ease.

It should be noted that results from the three hand-held prototype versions of the detector system 100 are not included in this report, as the software and calibration procedures varied and the localization results varied accordingly.

Figure 9:
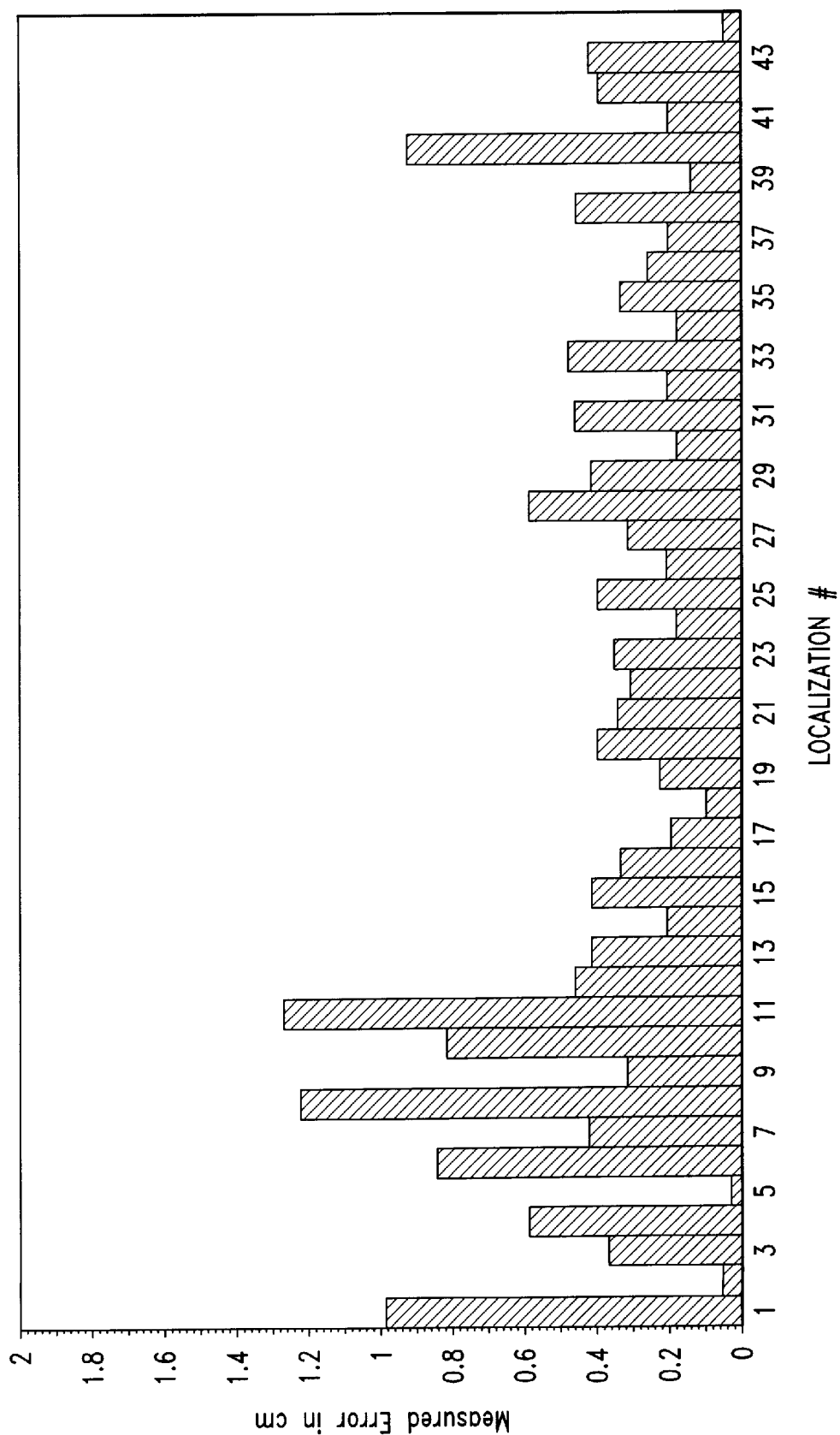
FIG. 9 is a graph illustrating the results of clinical testing of the system of FIG. 5A.

The accuracy of the PICC tip placement was determined by measuring the distance from the actual location of the magnet tagged tip, determined by the detector system 100, to the actual location of the catheter tip determined by fluoroscopy. The 44 localizations were performed in midclavicular and cranial vena caval positions, and there was no significant difference between the measured error at these locations (p=0.90). The mean measured error for 44 localizations in six animals, using the bench-top version of the detector system 100, was 0.40 cm with a standard deviation of ±0.29 cm. The results of the bench-top version of the detector system are illustrated in FIG. 9. The measured error ranged from 0.02 cm to 1.25 cm, but five out of six localizations with errors of greater than 0.6 cm were performed in the first twelve placements. As previously discussed, the early placements were complicated by difficulties aligning the fluoroscope jig with the detector system 100. As is readily apparent from FIG. 9, the alignment difficulties were solved after localization number twelve, with the resultant decrease in measurement error.

Conclusions

After the first eight localizations, the surgeon was asked to determine the anatomical position of the catheter tip by fluoroscopy without any input from other observers. After the magnet tip PICC was placed using the bench-top version of the detector system 100, the surgeon confirmed that the PICC was in the desired position in every localization.

The use of an external anatomical landmark in placing PICCs permits healthcare providers to insert the catheters in many different settings, from the home setting to outpatient clinics. The detector system successfully demonstrated that it could locate the tip of the tagged catheter within an average of 4 mm relative to an external landmark. The external landmarks used in this study do not correlate precisely with human landmarks, due to differences in interspecies anatomy, but the concept of placing a catheter at a prescribed landmark using the detector system 100 has been established.

The detector system 100 also permitted users to overcome difficulties in catheter insertions. In several cases during the study, the operator felt resistance at some point during the insertion and used the real-time position and orientation data to position the catheter correctly. This capability proved most useful when the catheter doubled back on itself, which is easily shown using the detector system 100 because the catheter tip stopped its forward progress and rolled into a new orientation. At this point in time, the operator withdrew the catheter until the tip of the image resumed its proper orientation, and the insertion was completed. Another valuable application is the ability to watch the image of the catheter tip as the catheter negotiates sharp angles and curves in the venous system. The investigator used this aspect of the detector system 100 while passing the catheter from the left cephalic vein to the left external jugular vein. The user felt considerable resistance that correlated with the rendering appearing to "bump" into a wall. By twisting and repositioning the catheter, it was eventually passed into the jugular vein, and the investigator felt comfortable that it was positioned correctly. Without immediate, real-time feedback, the user does not know if the catheter takes a wrong turn or kinks until the procedure is over and the patient has undergone radiographic verification. Thus, the present study illustrates the ability of the detector system 100 to accurately locate the catheter tip relative to an external landmark in an animal model, and lays the groundwork for proving its clinical efficacy in placing PICCs and other medical devices.

From the foregoing, it will be appreciated that, although specific embodiments of this invention have been described herein for purposes of illustration, various modifications may be made without deviating from the spirit and scope of the invention. Accordingly, the invention is not limited except by the appended claims.

What is claimed is:

1. A system for detecting a position of a magnet associated with an indwelling medical device from a measurement location on the surface of a patient, the system comprising:

a housing;

first, second, and third magnetic sensors supported by the housing, each of the magnetic sensors comprising sensor elements to detect magnetic field strength in three orthogonal directions, the first, second, and third magnetic sensors generating first, second, and third sets of signals, respectively, as a function of static magnetic field strength and direction due to the magnet;

a processor to calculate an estimated position of the magnet in a three-dimensional space and to calculate a predicted magnetic field strength for the first, second and third sensors based on the estimated position, the processor further calculating an actual magnetic field strength using the first, second, and third sets of signals and generating an error function based on a difference between the predicted magnetic field strength and the actual magnetic field strength; and a display providing a visual display of data related to the position of the magnet in the three-dimensional space using the error function.

2. The system of claim 1, further including a neural network to generate the estimated position, the neural network receiving the first, second and third sets of signals and generating the estimated position based thereon.

3. The system of claim 2 wherein the neural network includes a learn mode and an operational mode, the neural network functioning in the learn mode to receive a plurality of the first, second and third sets of signals and generating estimated positions for each of the plurality of sets of the first, second and third sets of signals, the neural network further receiving data related to an actual position of the magnet after generating each of the estimated positions and using the plurality of sets of the first, second and third sets of signals, the estimated position data and the actual position data to create rules for generating the estimated position data while functioning in the operational mode, the neural network functioning in the operational mode to receive the first, second and third sets of signals and to generate the estimated position of the magnet based on the first, second and third sets of signals and the rules created while functioning in the learn mode.

4. The system of claim 1 wherein the magnet has a magnetic dipole moment indicative of the orientation of the magnet and the detected magnetic dipole moment is displayed on the display to indicate the magnet orientation.

5. The system of claim 1 wherein the display is supported by the housing.

6. The system of claim 5 wherein the display is a two-dimensional display with at least a portion of the display being transparent to allow the user to view the surface of the patient beneath the transparent portion.

7. The system of claim 1 wherein the display is an external display spaced apart from the housing and electrically coupled to the processor.

8. The system of claim 7 for use with a imaging device capable of generating an image of the internal anatomy of the patient, wherein the display displays the image of the internal anatomy of the patient combined with the data related to the position of the magnet.

9. The system of claim 1 wherein the processor iteratively calculates the estimated position and the predicted magnetic field strength until the error function indicates that the predicted magnetic field strength matches the actual magnetic field strength within a predetermined tolerance.

10. The system of claim 9 wherein the processor performs a first iteration based on an initial estimated position, the system further including a neural network to generate the initial estimated position, the neural network receiving the first, second and third sets of signals and generating the initial estimated position based thereon.

11. The system of claim 1 wherein the display provides the visual display of data based on a single generation of the error function.

12. The system of claim 1 wherein the first, second, and third sensors are selected from a group of magnetic sensors comprising Hall-effect sensors, flux-gate sensors, wound-core inductive sensors, magnetic field gradient sensors, squid sensors, magneto-resistive sensors, and nuclear precession sensors.

13. The system of claim 1 for use in the presence of a magnetic field of the Earth wherein the processor subtracts a first selected one of the first, second, and third sets of signals from a second selected one of the first, second, and third sets of signals different from the first selected one of the first, second, and third sets of signals to cancel the effects of the Earth's magnetic field.

14. The system of claim 13, further including position detector to detect the position of the housing and generate position data related thereto, and a calibration processor to compensate for variations in the Earth's magnetic field resulting from movement of the housing to a new location, the calibration processor calculating the change in position of the housing based on the position data, calculating the actual magnetic field strength at the new location, and calculating the contribution to the actual magnetic field resulting from the magnet, the calibration processor further using a difference between the actual magnetic field strength at the new location and the contribution to the actual magnetic field resulting from the magnet to compensate for the effects of the Earth's magnetic field.

15. The system of claim 1, further including a calibration circuit to calibrate said first, second, and third magnetic sensors.

16. The system of claim 1, further including position detector to detect the position of the housing and generate position data related thereto, the system being operable to record the position of the housing at a plurality of locations selected by the user, the display providing a visual display of the selected locations combined with the data related to the position of the magnet.

17. A system for detecting a position of a magnet associated with an indwelling medical device from a measurement location on the surface of a patient, the system comprising:

a plurality of magnetic sensors, each oriented in a known direction and generating a set of signals as a function of static magnetic field strength and direction due to the magnet;

a processor to calculate an estimated position of the magnet in a three-dimensional space and to calculate values related to a predicted magnetic field strength for at least a portion of the plurality of sensors based on the estimated position, the processor further calculating values related to an actual magnetic field strength using the set of signals and determining values related to the location of the magnet based on a difference between the values related to predicted magnetic field strength and the values related to the actual magnetic field strength;

a position detector to determine the location of the magnetic sensors and to generate position data relating thereto;

a calibration processor to receive the position data and values related to the location of the magnet and to compensate for the effects of the Earth's magnetic field as the location of the magnetic sensors changes with respect to the patient; and a display providing a visual display of values related to the position of the magnet in the three-dimensional space.

18. The system of claim 17 wherein the calibration processor calculates the change in position of the magnetic sensors based on the position data, calculates the actual magnetic field strength at the new location, and calculates the contribution to the values related to the actual magnetic field resulting from the magnet, the calibration processor further using a difference between the values related to the actual magnetic field strength at the new location and the contribution to the values related to the actual magnetic field resulting from the magnet to compensate for the effects of the Earth's magnetic field.

19. The system of claim 17 wherein the processor iteratively calculates the estimated position and the values related to the predicted magnetic field strength until the values related to the predicted magnetic field strength matches the values related to the actual magnetic field strength within a predetermined tolerance.

20. The system of claim 19 wherein the processor performs a first iteration based on an initial estimated position, the system further including a neural network to generate the initial estimated position, the neural network receiving the first, second and third sets of signals and generating the initial estimated position based thereon.

21. The system of claim 17 wherein the processor calculates the position of the magnet based on a single calculation of the values related to the predicted magnetic field strength and the values related to the actual magnetic field strength.

22. The system of claim 17 wherein the processor calculates the estimated position using a mathematical equation representative of the magnetic field strength.

23. The system of claim 17 wherein the processor calculates the estimated position using a mathematical equation representative of a gradient of the magnetic field strength.

24. The system of claim 17 wherein the sensors are selected from a group of magnetic sensors comprising Hall-effect sensors, flux-gate sensors, wound-core inductive sensors, magnetic field gradient sensors, squid sensors, magneto-resistive sensors, and nuclear precession sensors.

25. The system of claim 17, further including a calibration circuit to calibrate the plurality of sensors.

26. The system of claim 17 wherein the processor calculates a cost function based on the difference between the values related to the predicted magnetic field strength and the values related to the measured value related to magnetic field strength, the processor further generating a minimum value for the cost function and analyzing the minimum value for the cost function with a predetermined minimum value, and generating a signal to the user to indicate whether the minimum value is above or below the predetermined minimum value.

27. A system for detecting a position of a magnet associated with an indwelling medical device from a measurement location on the surface of a patient, the system comprising:
   a plurality of magnetic sensors maintained in fixed position with respect to each other, each of the magnetic sensors being oriented in a known direction and generating signals as a function of static magnetic field strength and direction due to the magnet;
   a processor to calculate an estimated position of the magnet in a three-dimensional space and to calculate a predicted magnetic field strength for at least a portion of the plurality of sensors based on the estimated position, the processor further calculating an actual magnetic field strength for the portion of sensors using signals and generating an error function based on a difference between the predicted magnetic field strength and the actual magnetic field strength; and
   a display providing a visual display of data related to the position of the magnet in the three-dimensional space based on the error function.

28. The system of claim 27 wherein the plurality of magnetic sensors are oriented in three orthogonal directions, the sensors generating first, second, and third sets of signals, respectively, as a function of static magnetic field strength in the three orthogonal directions.

29. A method for detecting a position of a magnet associated with an indwelling medical device from a measurement location on the surface of a patient, the method comprising the steps of:
   positioning a plurality of magnetic sensors at predetermined locations with respect to the magnet;
   detecting a magnetic field at each of the plurality of sensors;
   generating a set of signals related to the detected magnetic field due to the magnet;
   calculating an estimated position of the magnet;
   calculating a predicted value related to the magnetic field for the plurality of sensors based on the estimated position;
   calculating an actual value related to the magnetic field using the sets of signals;
   comparing the predicted value related to the magnetic field with the actual value related to the magnetic field to determine the position of the magnet; and
   displaying data related to the position of the magnet.

30. The method of claim 29, further including the step of analyzing the set of signal using a neural network to thereby generate the estimated position based on the set of signals.

31. The method of claim 29, further including the steps of recalculating the estimated position and the predicted value related to the magnetic field until the predicted value related to the magnetic field matches the actual value related to the magnetic field within a predetermined tolerance.

32. The method of claim 31 wherein a first iteration is performed based on an initial estimated position, the method further including the step of analyzing the set of signal using a neural network to thereby generate the initial estimated position based on the set of signals.

33. The method of claim 29, further including the steps of altering the measurement location to thereby reposition the plurality of magnetic sensors and repeating the steps of detecting the magnetic field, generating a set of signals, calculating an estimated position, calculating a predicted value, calculating an actual value, comparing the predicted value with the actual value to determine the position of the magnet relative to the altered measurement location, and displaying data related to the position of the magnet relative to the altered measurement location.

34. The method of claim 29 wherein the plurality of sensors are selected from a group of magnetic sensors comprising Hall-effect sensors, flux-gate sensors, wound-core inductive sensors, magnetic field gradient sensors, squid sensors, magneto-resistive sensors, and nuclear precession sensors.

35. The method of claim 29 for use in the presence of a magnetic field of the Earth, the method further including the step of subtracting a selected one of the set of signals generated by a first of the plurality of magnetic sensors from a second selected one of the set of signals generated by a second of the plurality of magnetic sensors to cancel the effects of the Earth's magnetic field.

36. The method of claim 29, further including the steps of:
   detecting the position of the plurality of magnetic sensors resulting from movement of the plurality of magnetic sensors to a new location and generating position data related thereto;
   calculating the change in position of the plurality of magnetic sensors based on the position data;

calculating values related to the actual magnetic field strength at the new location;

calculating the contribution to values related to the actual magnetic field resulting from the magnet; and using a difference between the values related to actual magnetic field strength at the new location and the contribution to the actual magnetic field resulting from the magnet to compensate for the effects of the Earth's magnetic field resulting from movement of the plurality of magnetic sensors to the new location.

37. The method of claim 29 wherein the step of displaying uses an external display spaced apart from the magnetic sensors.

38. The method of claim 28 for use with a imaging device capable of generating an image of the internal anatomy of the patient, the method further including the step of the displaying the image of the internal anatomy of the patient combined with the data related to the position of the magnet.

39. The method of claim 29, further including the steps of:

detecting the position the magnetic sensors and generating position data related thereto;

recording the positions of the magnetic sensors at a plurality of locations selected by the user; and displaying a visual display of the selected locations combined with the data related to the position of the magnet.

* * * * *

UNITED STATES PATENT AND TRADEMARK OFFICE
CERTIFICATE OF CORRECTION

PATENT NO. : 6,129,668
DATED : October 10, 2000
INVENTOR(S) : David R. Haynor

It is certified that error appears in the above-identified patent and that said Letters Patent is hereby corrected as shown below:

Claim 38, column 29,
Line 14, "The method of claim 28" should read -- The method of Claim 37 --.

Signed and Sealed this

Twenty-third Day of October, 2001

Attest:

NICHOLAS P. GODICI
Attesting Officer    Acting Director of the United States Patent and Trademark Office